US012570700B2

(12) United States Patent
Lee et al.

(10) Patent No.: US 12,570,700 B2
(45) Date of Patent: Mar. 10, 2026

(54) SARS-CoV-2 SPIKE RECEPTOR BINDING DOMAIN AND COMPOSITIONS AND METHODS THEREOF

(71) Applicant: REGENTS OF THE UNIVERSITY OF MINNESOTA, Minneapolis, MN (US)

(72) Inventors: Frank Jonathan Lee, Minneapolis, MN (US); Yushun Wan, Chongqing City (CN); Jian Shang, Zhengzhou City (CN)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 706 days.

(21) Appl. No.: 17/918,835

(22) PCT Filed: Mar. 25, 2021

(86) PCT No.: PCT/US2021/024176
§ 371 (c)(1),
(2) Date: Oct. 13, 2022

(87) PCT Pub. No.: WO2021/211279
PCT Pub. Date: Oct. 21, 2021

(65) Prior Publication Data

US 2023/0146256 A1 May 11, 2023

Related U.S. Application Data

(60) Provisional application No. 63/011,761, filed on Apr. 17, 2020.

(51) Int. Cl.
*C07K 14/005* (2006.01)
*A61K 39/00* (2006.01)
*G01N 33/569* (2006.01)

(52) U.S. Cl.
CPC ..... *C07K 14/005* (2013.01); *G01N 33/56983* (2013.01); *A61K 39/00* (2013.01); *C07K 2319/02* (2013.01); *C07K 2319/21* (2013.01); *C12N 2770/20022* (2013.01); *G01N 2333/165* (2013.01)

(58) Field of Classification Search
None
See application file for complete search history.

(56) References Cited

U.S. PATENT DOCUMENTS

| | | | |
|---|---|---|---|
| 7,888,102 | B2 | 2/2011 | Van et al. |
| 2008/0063664 | A1 | 3/2008 | Hsiao et al. |
| 2019/0328865 | A1 | 10/2019 | Du et al. |
| 2022/0001006 | A1 | 1/2022 | Lee et al. |
| 2022/0324918 | A1 | 10/2022 | Lee et al. |
| 2023/0346916 | A1 | 11/2023 | Du et al. |

FOREIGN PATENT DOCUMENTS

| | | | |
|---|---|---|---|
| CN | 1884303 | A | 12/2006 |
| WO | 2015164865 | A1 | 10/2015 |
| WO | 2018215766 | A1 | 11/2018 |
| WO | 2022015668 | A1 | 1/2022 |

OTHER PUBLICATIONS

U.S. Appl. No. 17/361,486, US 2022-0001006.
Du, L. , et al., "Receptor-binding domain of SARS-CoV spike protein induces long-term protective immunity in an animal model", Vaccine 25(15), 2832-2838 (2007).
Geng, Q, et al., "Novel virus-like nanoparticle vaccine effectively protects animal model from SARS-CoV-2 infection", PLoS Pathog 17 (9), e1009897, 1-20 (2021).
Hoffmann, M , et al., "SARS-CoV-2 Cell Entry Depends on ACE2 and TMPRSS2 and Is Blocked by a Clinically Proven Protease Inhibitor", Cell 181 (2), 271-280 (2020).
Jiang, S, et al., "An emerging coronavirus causing pneumonia outbreak in Wuhan, China: calling for developing therapeutic and prophylactic strategies", Emerging Microbes & Infections 9, 275-277 (2020).
Jiang, S , et al., "Receptor-binding domains of spike proteins of emerging or re-emerging viruses as targets for development of antiviral vaccines", Emerg Microbes Infect (8), e13.doi: 10.1038/emi.2012.1, 8 pages (2012).
Joyce, M , et al., "A Cryptic Site of Vulnerability on the Receptor Binding Domain of the SARS-CoV-2 Spike Glycoprotein", bioRxiv preprint doi: https://doi.org/10.1101/2020.03.15.992883, 32 pages (2020).
Ju, B , et al., "Potent human neutralizing antibodies elicited 1 by SARS-CoV-2 infection", bioRxiv preprint doi: https://doi.org/10.1101/2020.03.21.990770, 42 pages (2020).
Lan, J , et al., "Structure of the SARS-CoV- spike receptor-binding domain bound to the ACE2 receptor", Nature 581, 215-220 (2020).
Li, W, et al., "Identification of sialic acid-binding function for the Middle East respiratory syndrome coronavirus spike glycoprotein", Proc Natl Acad Sci 114 (40), E8508-E8517 (2017).
Li, F , "Structural Analysis of Major Species Barriers between Humans and Palm Civets for Severe Acute Respiratory Syndrome Coronavirus Infections", Journal of Virology 82 (14), 6984-6991 (2008).
Li, F , et al., "Structure of SARS Coronavirus Spike Receptor-Binding Domain Complexed with Receptor", Science 309, 1864-1868 (2005).
Lopez-Sagaseta, J. , "Receptor-binding domain of SARS-CoV spike protein induces long-term protective immunity in an animal model", Computational and Structural Biotechnology Journal 14, 58-68(2015).
Lu, L , et al., "Structure-based discovery of Middle East respiratory syndrome coronavirus fusion inhibitor", Nature Communications 5 (3067), DOI:10.1038/ncomms4067, 12 pages (2014).

(Continued)

*Primary Examiner* — Manjunath N Rao
*Assistant Examiner* — Jae W Lee
(74) *Attorney, Agent, or Firm* — Viksnins Harris Padys Malen LLP

(57) ABSTRACT

The present disclosure provides an isolated or purified SARS-CoV-2 Receptor Binding Domain (RBD) polypeptide and cells for producing such a polypeptide, as well as compositions and methods thereof.

8 Claims, 5 Drawing Sheets

Specification includes a Sequence Listing.

(56) References Cited

OTHER PUBLICATIONS

Ou, X, et al., "Characterization of spike glycoprotein of SARS-CoV-2 on virus entry and its immune cross-reactivity with SARS-CoV", Nature Communications 11, 1620, 1-12, Supplementary Information, 16 pages (2020).
Pallesen, J , et al., "Immunogenicity and structures of a rationally designed prefusion MERS-CoV spike antigen", PNAS, doi/10.1073/pnas.1707304114, E7348-E7357 (2017).
Patent Cooperation Treaty , International Search Report and Written Opinion for PCT/US2021/024176, 16 pages, dated Aug. 2, 2021.
Pati, R, et al., "Nanoparticle Vaccines Against Infectious Diseases", Front Immunol 9, 2224, 16 pages (2018).
Portolano, N, "Recombinant protein expression for structural biology in HEK 293F suspension cells: a novel and accessible approach", J Vis Exp (92), e51897, doi:10.3791/51897, 1-8 (2014).
Sekimukai, H , et al., "Gold nanoparticle-adjuvanted S protein induces a strong antigen-specific IgG response against severe acute respiratory syndrome-related coronavirus infection, but fails to induce protective antibodies and limit eosinophilic infiltration in lungs", Microbiology and Immunology 64, 33-51 (2020) (Epub Nov. 2019).
Shang, J , et al., "Cell entry mechanisms of SARS-CoV-2", PNAS 117 (21), 11727-11734 (2020).
Shang, J , et al., "Structural basis of receptor recognition by SARS-CoV-2", Nature 581, 221-224, 18 pages (2020).
Tai, W, et al., "Characterization of the receptor-binding domain (RBD) of 2019 novel coronavirus: implication for development of RBD protein as a viral attachment inhibitor and vaccine", Cellular & Molecular Immunology 17, 613-620 (2020).
Walls, A, et al., "Elicitation of Potent Neutralizing Antibody Responses by Designed Protein Nanoparticle Vaccines for SARS-CoV-2", Cell 183 (5), 1367-1382, e1317 (2020).
Walls, A, et al., "Structure, Function, and Antigenicity of the SARS-CoV-2 Spike Glycoprotein", Cell 180, 281-292 (2020).
Wang, X, et al., "SARS-CoV-2 infects T lymphocytes through its spike protein-mediated membrane fusion", Cell Mol Immunol, https://doi.org/10.1038/s41423-020-0424-9, 3 pages and two retraction notices 2 pages (2020).
Wang, Q, et al., "Structural and Functional Basis of SARS-CoV-2 Entry by Using Human ACE2", Cell 181, 894-904 (2020).
Wu, K, et al., "Crystal structure of NL63 respiratory coronavirus receptor-binding domain complexed with its human receptor", PNAS 106 (47), 19970-19974 (2009).
Wu, K, et al., "Mechanisms of Host Receptor Adaptation by Severe Acute Respiratory Syndrome Coronavirus", Journal of Biological Chemistry 287 (12), 8904-8911 (2012).
Xia, S, et al., "A pan-coronavirus fusion inhibitor targeting the HR1 domain of human coronavirus spike", Sci Adv 5 (4), eaav4580, doi: 10.1126/sciadv.aav4580, 1-15 (2019).
Ye, G, et al., "The Development of a Novel Nanobody Therapeutic for SARS-CoV-2", bioRxiv preprint , https://doi.org/10.1101/2020.11.17.386532, 1-48 (2020).
Zhao, R , et al., "Serological diagnostic kit of SARS-CoV-2 antibodies using CHO-expressed full-length SARS-CoV-2 S1 proteins", medRxiv preprint doi: https://doi.org/10.1101/2020.03.26.20042184, 24 pages (2020).

Protein Sequence for SARS-CoV-2 RBD (with a C-terminal His8 tag):

RVQPTESIVRFPNITNLCPFGEVFNATRFASVYAWNRKRISNCVADYSVLYNSASFSTFKCYGVSPTK
LNDLCFTNVYADSFVIRGDEVRQIAPGQTGKIADYNYKLPDDFTGCVIAWNSNNLDSKVGGNYNYLY
RLFRKSNLKPFERDISTEIYQAGSTPCNGVEGFNCYFPLQSYGFQPTNGVGYQPYRVVVLSFELLH
APATVCGPKKSTNLVKGSHHHHHHHH

SDS-PAGE gel stained by Coomassie Blue

SEQUENCE LISTING

<160> NUMBER OF SEQ ID NOS: 42

<210> SEQ ID NO 1
<211> LENGTH: 753
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 1

```
atggacgcca tgaagagggg cctgtgctgc gtgctgctgc tgtgcggcgc cgtgttcgtg     60
agcgccagcc gcgtgcagcc aaccgagagc atcgtgcgct tccccaatat caccaacctg    120
tgcccattcg gcgaggtgtt caacgctacc aggttcgcca gcgtgtacgc ttggaatcgc    180
aagcgcatct ccaactgcgt ggccgactac agcgtgctgt acaactccgc cagcttctcc    240
accttcaagt gctacggcgt gtcccccacc aagctgaatg atctgtgctt caccaacgtg    300
tacgccgata gcttcgtgat caggggcgac gaggtgcgcc agatcgctcc aggacagacc    360
ggcaagatcg ctgactacaa ttacaagctg cccgacgatt tcaccggctg cgtgatcgcc    420
tggaactcca acaatctgga tagcaaagtg ggcggcaact acaattacct gtaccgcctg    480
ttccgcaagt ccaatctgaa gccattcgag cgcgacatct ccaccgagat ctaccaggct    540
ggaagcaccc catgcaatgg agtggagggc ttcaactgct acttccccct gcagagctac    600
ggcttccagc caaccaacgg agtgggatac cagccataca gggtggtggt gctgtccttc    660
gagctgctgc acgctccagc taccgtgtgc ggaccaaaga agagcaccaa tctggtgaag    720
ggatcccacc atcaccatca ccatcaccat tag                                 753
```

<210> SEQ ID NO 2
<211> LENGTH: 217
<212> TYPE: PRT
<213> ORGANISM: Severe acute respiratory syndrome coronavirus 2

<400> SEQUENCE: 2

```
Arg Val Gln Pro Thr Glu Ser Ile Val Arg Phe Pro Asn Ile Thr Asn
1               5                   10                  15

Leu Cys Pro Phe Gly Glu Val Phe Asn Ala Thr Arg Phe Ala Ser Val
            20                  25                  30

Tyr Ala Trp Asn Arg Lys Arg Ile Ser Asn Cys Val Ala Asp Tyr Ser
        35                  40                  45

Val Leu Tyr Asn Ser Ala Ser Phe Ser Thr Phe Lys Cys Tyr Gly Val
    50                  55                  60

Ser Pro Thr Lys Leu Asn Asp Leu Cys Phe Thr Asn Val Tyr Ala Asp
65                  70                  75                  80

Ser Phe Val Ile Arg Gly Asp Glu Val Arg Gln Ile Ala Pro Gly Gln
                85                  90                  95

Thr Gly Lys Ile Ala Asp Tyr Asn Tyr Lys Leu Pro Asp Asp Phe Thr
            100                 105                 110

Gly Cys Val Ile Ala Trp Asn Ser Asn Asn Leu Asp Ser Lys Val Gly
        115                 120                 125

Gly Asn Tyr Asn Tyr Leu Tyr Arg Leu Phe Arg Lys Ser Asn Leu Lys
    130                 135                 140

Pro Phe Glu Arg Asp Ile Ser Thr Glu Ile Tyr Gln Ala Gly Ser Thr
145                 150                 155                 160

Pro Cys Asn Gly Val Glu Gly Phe Asn Cys Tyr Phe Pro Leu Gln Ser
                165                 170                 175

Tyr Gly Phe Gln Pro Thr Asn Gly Val Gly Tyr Gln Pro Tyr Arg Val
            180                 185                 190

Val Val Leu Ser Phe Glu Leu Leu His Ala Pro Ala Thr Val Cys Gly
        195                 200                 205

Pro Lys Lys Ser Thr Asn Leu Val Lys
    210                 215
```

<210> SEQ ID NO 3
<211> LENGTH: 227
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 3

```
Arg Val Gln Pro Thr Glu Ser Ile Val Arg Phe Pro Asn Ile Thr Asn
1               5                   10                  15

Leu Cys Pro Phe Gly Glu Val Phe Asn Ala Thr Arg Phe Ala Ser Val
            20                  25                  30

Tyr Ala Trp Asn Arg Lys Arg Ile Ser Asn Cys Val Ala Asp Tyr Ser
        35                  40                  45

Val Leu Tyr Asn Ser Ala Ser Phe Ser Thr Phe Lys Cys Tyr Gly Val
    50                  55                  60

Ser Pro Thr Lys Leu Asn Asp Leu Cys Phe Thr Asn Val Tyr Ala Asp
65                  70                  75                  80

Ser Phe Val Ile Arg Gly Asp Glu Val Arg Gln Ile Ala Pro Gly Gln
                85                  90                  95

Thr Gly Lys Ile Ala Asp Tyr Asn Tyr Lys Leu Pro Asp Asp Phe Thr
            100                 105                 110

Gly Cys Val Ile Ala Trp Asn Ser Asn Asn Leu Asp Ser Lys Val Gly
        115                 120                 125

Gly Asn Tyr Asn Tyr Leu Tyr Arg Leu Phe Arg Lys Ser Asn Leu Lys
    130                 135                 140

Pro Phe Glu Arg Asp Ile Ser Thr Glu Ile Tyr Gln Ala Gly Ser Thr
145                 150                 155                 160

Pro Cys Asn Gly Val Glu Gly Phe Asn Cys Tyr Phe Pro Leu Gln Ser
                165                 170                 175

Tyr Gly Phe Gln Pro Thr Asn Gly Val Gly Tyr Gln Pro Tyr Arg Val
            180                 185                 190

Val Val Leu Ser Phe Glu Leu Leu His Ala Pro Ala Thr Val Cys Gly
        195                 200                 205

Pro Lys Lys Ser Thr Asn Leu Val Lys Gly Ser His His His His His
    210                 215                 220

His His His
225
```

<210> SEQ ID NO 4
<211> LENGTH: 250
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 4

```
Met Asp Ala Met Lys Arg Gly Leu Cys Cys Val Leu Leu Leu Cys Gly
1               5                   10                  15

Ala Val Phe Val Ser Ala Ser Arg Val Gln Pro Thr Glu Ser Ile Val
            20                  25                  30

Arg Phe Pro Asn Ile Thr Asn Leu Cys Pro Phe Gly Glu Val Phe Asn
        35                  40                  45

Ala Thr Arg Phe Ala Ser Val Tyr Ala Trp Asn Arg Lys Arg Ile Ser
    50                  55                  60
```

```
Asn Cys Val Ala Asp Tyr Ser Val Leu Tyr Asn Ser Ala Ser Phe Ser
65                  70                  75                  80

Thr Phe Lys Cys Tyr Gly Val Ser Pro Thr Lys Leu Asn Asp Leu Cys
                85                  90                  95

Phe Thr Asn Val Tyr Ala Asp Ser Phe Val Ile Arg Gly Asp Glu Val
            100                 105                 110

Arg Gln Ile Ala Pro Gly Gln Thr Gly Lys Ile Ala Asp Tyr Asn Tyr
        115                 120                 125

Lys Leu Pro Asp Asp Phe Thr Gly Cys Val Ile Ala Trp Asn Ser Asn
    130                 135                 140

Asn Leu Asp Ser Lys Val Gly Gly Asn Tyr Asn Tyr Leu Tyr Arg Leu
145                 150                 155                 160

Phe Arg Lys Ser Asn Leu Lys Pro Phe Glu Arg Asp Ile Ser Thr Glu
                165                 170                 175

Ile Tyr Gln Ala Gly Ser Thr Pro Cys Asn Gly Val Glu Gly Phe Asn
            180                 185                 190

Cys Tyr Phe Pro Leu Gln Ser Tyr Gly Phe Gln Pro Thr Asn Gly Val
        195                 200                 205

Gly Tyr Gln Pro Tyr Arg Val Val Val Leu Ser Phe Glu Leu Leu His
    210                 215                 220

Ala Pro Ala Thr Val Cys Gly Pro Lys Lys Ser Thr Asn Leu Val Lys
225                 230                 235                 240

Gly Ser His His His His His His His His
                245                 250
```

<210> SEQ ID NO 5
<211> LENGTH: 237
<212> TYPE: PRT
<213> ORGANISM: Severe acute respiratory syndrome coronavirus 2

<400> SEQUENCE: 5

```
Glu Lys Gly Ile Tyr Gln Thr Ser Asn Phe Arg Val Gln Pro Thr Glu
1               5                   10                  15

Ser Ile Val Arg Phe Pro Asn Ile Thr Asn Leu Cys Pro Phe Gly Glu
            20                  25                  30

Val Phe Asn Ala Thr Arg Phe Ala Ser Val Tyr Ala Trp Asn Arg Lys
        35                  40                  45

Arg Ile Ser Asn Cys Val Ala Asp Tyr Ser Val Leu Tyr Asn Ser Ala
    50                  55                  60

Ser Phe Ser Thr Phe Lys Cys Tyr Gly Val Ser Pro Thr Lys Leu Asn
65                  70                  75                  80

Asp Leu Cys Phe Thr Asn Val Tyr Ala Asp Ser Phe Val Ile Arg Gly
                85                  90                  95

Asp Glu Val Arg Gln Ile Ala Pro Gly Gln Thr Gly Lys Ile Ala Asp
            100                 105                 110

Tyr Asn Tyr Lys Leu Pro Asp Asp Phe Thr Gly Cys Val Ile Ala Trp
        115                 120                 125

Asn Ser Asn Asn Leu Asp Ser Lys Val Gly Gly Asn Tyr Asn Tyr Leu
    130                 135                 140

Tyr Arg Leu Phe Arg Lys Ser Asn Leu Lys Pro Phe Glu Arg Asp Ile
145                 150                 155                 160

Ser Thr Glu Ile Tyr Gln Ala Gly Ser Thr Pro Cys Asn Gly Val Glu
                165                 170                 175

Gly Phe Asn Cys Tyr Phe Pro Leu Gln Ser Tyr Gly Phe Gln Pro Thr
```

-continued

```
            180                 185                 190

Asn Gly Val Gly Tyr Gln Pro Tyr Arg Val Val Val Leu Ser Phe Glu
        195                 200                 205

Leu Leu His Ala Pro Ala Thr Val Cys Gly Pro Lys Lys Ser Thr Asn
    210                 215                 220

Leu Val Lys Asn Lys Cys Val Asn Phe Asn Phe Asn Gly
225                 230                 235


<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      8xHis tag

<400> SEQUENCE: 6

His His His His His His His His
1               5


<210> SEQ ID NO 7
<211> LENGTH: 23
<212> TYPE: PRT
<213> ORGANISM: Unknown
<220> FEATURE:
<223> OTHER INFORMATION: Description of Unknown:
      tPA signal peptide

<400> SEQUENCE: 7

Met Asp Ala Met Lys Arg Gly Leu Cys Cys Val Leu Leu Leu Cys Gly
1               5                   10                  15

Ala Val Phe Val Ser Ala Ser
            20


<210> SEQ ID NO 8
<211> LENGTH: 3819
<212> TYPE: DNA
<213> ORGANISM: Severe acute respiratory syndrome coronavirus 2

<400> SEQUENCE: 8

atgtttgtct tcctggtcct gctgcctctg gtctcgtctc agtgcgtgaa cctgactact     60

agaacccagc tgcctcctgc ctatactaac tccttcaccc gcggcgtgta ctacccagac    120

aaggtgttcc gcagctccgt gctgcactcc acccaggatc tgttcctgcc cttcttcagc    180

aacgtgacct ggttccacgc catccacgtg agcggcacca atggcaccaa gcggttcgac    240

aatcccgtgc tgccattcaa cgatggcgtg tacttcgcct ccaccgagaa gagcaacatc    300

atccgcggct ggatcttcgg caccaccctg gactccaaga cccagagcct gctgatcgtg    360

aacaatgcca ccaacgtggt catcaaggtg tgcgagttcc agttctgcaa tgatccattc    420

ctgggcgtgt actaccacaa gaacaataag tcctggatgg agagcgagtt ccgcgtgtac    480

agctccgcca acaattgcac cttcgagtac gtgtcccagc ccttcctgat ggacctggag    540

ggcaagcagg gcaatttcaa gaacctgcgc gagttcgtgt tcaagaatat cgatggctac    600

ttcaagatct actccaagca cacccccatc aacctggtgc gcgacctgcc acagggcttc    660

agcgccctgg agccactggt ggatctgcca atcggcatca acatcaccag gttccagacc    720

ctgctggccc tgcaccgcag ctacctgacc ccaggcgaca gctccagcgg atggaccgct    780

ggagctgctg cctactacgt gggctacctg cagccccgca ccttcctgct gaagtacaac    840

gagaatggca ccatcaccga cgccgtggat tgcgccctgg atccactgtc cgagacaaag    900
```

-continued

```
tgcaccctga agagcttcac cgtggagaag ggcatctacc agacctccaa tttccgcgtg    960
cagccaaccg agagcatcgt gcgcttcccc aatatcacca acctgtgccc attcggcgag   1020
gtgttcaacg ctaccaggtt cgccagcgtg tacgcttgga atcgcaagcg catctccaac   1080
tgcgtggccg actacagcgt gctgtacaac tccgccagct tctccacctt caagtgctac   1140
ggcgtgtccc ccaccaagct gaatgatctg tgcttcacca acgtgtacgc cgatagcttc   1200
gtgatcaggg gcgacgaggt gcgccagatc gctccaggac agaccggcaa gatcgctgac   1260
tacaattaca agctgcccga cgatttcacc ggctgcgtga tcgcctggaa ctccaacaat   1320
ctggatagca aagtgggcgg caactacaat tacctgtacc gcctgttccg caagtccaat   1380
ctgaagccat tcgagcgcga catctccacc gagatctacc aggctggaag caccccatgc   1440
aatggagtgg agggcttcaa ctgctacttc cccctgcaga gctacggctt ccagccaacc   1500
aacggagtgg gataccagcc atacagggtg gtggtgctgt ccttcgagct gctgcacgct   1560
ccagctaccg tgtgcggacc aaagaagagc accaatctgg tgaagaacaa gtgcgtgaac   1620
ttcaatttca acggcctgac cggaaccggc gtgctgaccg agtccaacaa gaagttcctg   1680
ccattccagc agttcggaag ggacatcgct gataccaccg acgccgtgcg cgacccacag   1740
accctggaga tcctggatat caccccatgc tccttcggcg gcgtgagcgt gatcacccca   1800
ggaaccaata ccagcaacca ggtggccgtg ctgtaccagg acgtgaattg caccgaggtg   1860
ccagtggcta tccacgctga tcagctgacc ccaacctggc gcgtgtacag caccggatcc   1920
aacgtgttcc agacccgcgc cggatgcctg atcggagctg agcacgtgaa caattcctac   1980
gagtgcgaca tcccaatcgg agctggaatc tgcgccagct accagaccca gaccaactcc   2040
ccaaggaggg ctcgcagcgt ggccagccag tccatcatcg cctacaccat gtccctgggc   2100
gccgagaata gcgtggccta cagcaacaat tccatcgcca tcccaaccaa cttcaccatc   2160
tccgtgacca ccgagatcct gcccgtgtcc atgaccaaga ccagcgtgga ctgcaccatg   2220
tacatctgcg gcgattccac cgagtgcagc aacctgctgc tgcagtacgg cagcttctgc   2280
acccagctga atcgcgccct gaccggaatc gctgtggagc aggataagaa cacccaggag   2340
gtgttcgccc aggtgaagca gatctacaag acccccccaa tcaaggactt cggcggcttc   2400
aatttcagcc agatcctgcc cgatccaagc aagccctcca agcgcagctt catcgaggac   2460
ctgctgttca acaaggtgac cctggccgat gccggcttca tcaagcagta cggcgattgc   2520
ctgggcgaca tcgctgcccg cgacctgatc tgcgcccaga agttcaatgg cctgaccgtg   2580
ctgccaccac tgctgaccga tgagatgatc gctcagtaca cctccgccct gctggccgga   2640
accatcacca gcggatggac cttcggcgct ggagccgccc tgcagatccc cttcgccatg   2700
cagatggcct accgcttcaa cggcatcggc gtgacccaga atgtgctgta cgagaaccag   2760
aagctgatcg ccaatcagtt caactccgcc atcggcaaga tccaggactc cctgtccagc   2820
accgccagcg ccctgggcaa gctgcaggat gtggtgaatc agaacgccca ggccctgaat   2880
accctggtga agcagctgtc cagcaacttc ggcgccatct ccagcgtgct gaatgatatc   2940
ctgagccgcc tggacaaggt ggaggctgag gtgcagatcg ataggctgat caccggccgc   3000
ctgcagtccc tgcagaccta cgtgacccag cagctgatca gggctgctga gatcagggcc   3060
agcgccaatc tggctgctac caagatgtcc gagtgcgtgc tgggacagag caagagggtg   3120
gacttctgcg gcaagggcta ccacctgatg tccttcccac agagcgcccc acacggagtg   3180
gtgttcctgc acgtgaccta cgtgccagcc caggagaaga acttcaccac cgctccagct   3240
```

-continued

```
atctgccacg atggcaaggc tcacttccca cgcgagggcg tgttcgtgtc caacggcacc   3300

cactggttcg tgacccagcg caatttctac gagccccaga tcatcaccac cgacaatacc   3360

ttcgtgagcg gcaactgcga cgtggtcatc ggaatcgtga acaataccgt gtacgatccc   3420

ctgcagccag agctggactc cttcaaggag gagctggata agtacttcaa gaatcacacc   3480

agccccgacg tggatctggg cgacatctcc ggcatcaatg ccagcgtggt gaacatccag   3540

aaggagatcg accgcctgaa cgaggtggcc aagaatctga acgagtccct gatcgatctg   3600

caggagctgg gcaagtacga gcagtacatc aagtggccat ggtacatctg gctgggcttc   3660

atcgccggcc tgatcgccat cgtgatggtg accatcatgc tgtgctgcat gacctcctgc   3720

tgcagctgcc tgaagggctg ctgctcctgc ggcagctgct gcaagttcga tgaggacgat   3780

agcgagcccg tgctgaaggg cgtcaaactg cactataca                          3819
```

```
<210> SEQ ID NO 9
<211> LENGTH: 1273
<212> TYPE: PRT
<213> ORGANISM: Severe acute respiratory syndrome coronavirus 2

<400> SEQUENCE: 9

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270
```

-continued

```
Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
```

-continued

```
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
            980                 985                 990

Ile Asp Arg Leu Ile Thr Gly Arg  Leu Gln Ser Leu Gln  Thr Tyr Val
        995                 1000                1005

Thr Gln  Gln Leu Ile Arg Ala  Ala Glu Ile Arg Ala  Ser Ala Asn
    1010                1015                1020

Leu Ala  Ala Thr Lys Met Ser  Glu Cys Val Leu Gly  Gln Ser Lys
    1025                1030                1035

Arg Val  Asp Phe Cys Gly Lys  Gly Tyr His Leu Met  Ser Phe Pro
    1040                1045                1050

Gln Ser  Ala Pro His Gly Val  Val Phe Leu His Val  Thr Tyr Val
    1055                1060                1065

Pro Ala  Gln Glu Lys Asn Phe  Thr Thr Ala Pro Ala  Ile Cys His
    1070                1075                1080

Asp Gly  Lys Ala His Phe Pro  Arg Glu Gly Val Phe  Val Ser Asn
    1085                1090                1095

Gly Thr  His Trp Phe Val Thr  Gln Arg Asn Phe Tyr  Glu Pro Gln
    1100                1105                1110
```

Ile Ile Thr Thr Asp Asn Thr Phe Val Ser Gly Asn Cys Asp Val
1115 1120 1125

Val Ile Gly Ile Val Asn Asn Thr Val Tyr Asp Pro Leu Gln Pro
1130 1135 1140

Glu Leu Asp Ser Phe Lys Glu Glu Leu Asp Lys Tyr Phe Lys Asn
1145 1150 1155

His Thr Ser Pro Asp Val Asp Leu Gly Asp Ile Ser Gly Ile Asn
1160 1165 1170

Ala Ser Val Val Asn Ile Gln Lys Glu Ile Asp Arg Leu Asn Glu
1175 1180 1185

Val Ala Lys Asn Leu Asn Glu Ser Leu Ile Asp Leu Gln Glu Leu
1190 1195 1200

Gly Lys Tyr Glu Gln Tyr Ile Lys Trp Pro Trp Tyr Ile Trp Leu
1205 1210 1215

Gly Phe Ile Ala Gly Leu Ile Ala Ile Val Met Val Thr Ile Met
1220 1225 1230

Leu Cys Cys Met Thr Ser Cys Cys Ser Cys Leu Lys Gly Cys Cys
1235 1240 1245

Ser Cys Gly Ser Cys Cys Lys Phe Asp Glu Asp Asp Ser Glu Pro
1250 1255 1260

Val Leu Lys Gly Val Lys Leu His Tyr Thr
1265 1270

<210> SEQ ID NO 10
<211> LENGTH: 197
<212> TYPE: PRT
<213> ORGANISM: Severe acute respiratory syndrome coronavirus 2

<400> SEQUENCE: 10

Phe Pro Asn Ile Thr Asn Leu Cys Pro Phe Gly Glu Val Phe Asn Ala
1 5 10 15

Thr Arg Phe Ala Ser Val Tyr Ala Trp Asn Arg Lys Arg Ile Ser Asn
20 25 30

Cys Val Ala Asp Tyr Ser Val Leu Tyr Asn Ser Ala Ser Phe Ser Thr
35 40 45

Phe Lys Cys Tyr Gly Val Ser Pro Thr Lys Leu Asn Asp Leu Cys Phe
50 55 60

Thr Asn Val Tyr Ala Asp Ser Phe Val Ile Arg Gly Asp Glu Val Arg
65 70 75 80

Gln Ile Ala Pro Gly Gln Thr Gly Lys Ile Ala Asp Tyr Asn Tyr Lys
85 90 95

Leu Pro Asp Asp Phe Thr Gly Cys Val Ile Ala Trp Asn Ser Asn Asn
100 105 110

Leu Asp Ser Lys Val Gly Gly Asn Tyr Asn Tyr Leu Tyr Arg Leu Phe
115 120 125

Arg Lys Ser Asn Leu Lys Pro Phe Glu Arg Asp Ile Ser Thr Glu Ile
130 135 140

Tyr Gln Ala Gly Ser Thr Pro Cys Asn Gly Val Glu Gly Phe Asn Cys
145 150 155 160

Tyr Phe Pro Leu Gln Ser Tyr Gly Phe Gln Pro Thr Asn Gly Val Gly
165 170 175

Tyr Gln Pro Tyr Arg Val Val Val Leu Ser Phe Glu Leu Leu His Ala
180 185 190

Pro Ala Thr Val Cys

195

<210> SEQ ID NO 11
<211> LENGTH: 10
<212> TYPE: PRT
<213> ORGANISM: Severe acute respiratory syndrome coronavirus 2

<400> SEQUENCE: 11

Arg Val Gln Pro Thr Glu Ser Ile Val Arg
1 5 10

<210> SEQ ID NO 12
<211> LENGTH: 10
<212> TYPE: PRT
<213> ORGANISM: Severe acute respiratory syndrome coronavirus 2

<400> SEQUENCE: 12

Gly Pro Lys Lys Ser Thr Asn Leu Val Lys
1 5 10

<210> SEQ ID NO 13
<211> LENGTH: 10
<212> TYPE: PRT
<213> ORGANISM: Severe acute respiratory syndrome coronavirus 2

<400> SEQUENCE: 13

Glu Lys Gly Ile Tyr Gln Thr Ser Asn Phe
1 5 10

<210> SEQ ID NO 14
<211> LENGTH: 10
<212> TYPE: PRT
<213> ORGANISM: Severe acute respiratory syndrome coronavirus 2

<400> SEQUENCE: 14

Asn Lys Cys Val Asn Phe Asn Phe Asn Gly
1 5 10

<210> SEQ ID NO 15
<211> LENGTH: 7
<212> TYPE: PRT
<213> ORGANISM: Severe acute respiratory syndrome coronavirus 2

<400> SEQUENCE: 15

Lys Ser Thr Asn Leu Val Lys
1 5

<210> SEQ ID NO 16
<211> LENGTH: 6
<212> TYPE: PRT
<213> ORGANISM: Severe acute respiratory syndrome coronavirus 2

<400> SEQUENCE: 16

Ser Thr Asn Leu Val Lys
1 5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 17

-continued

Asn Lys Cys Val Asn Phe Ser
1               5

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Asn Lys Cys Val Asn Phe
1               5

<210> SEQ ID NO 19
<211> LENGTH: 9
<212> TYPE: PRT
<213> ORGANISM: Severe acute respiratory syndrome coronavirus 2

<400> SEQUENCE: 19

Val Gln Pro Thr Glu Ser Ile Val Arg
1               5

<210> SEQ ID NO 20
<211> LENGTH: 8
<212> TYPE: PRT
<213> ORGANISM: Severe acute respiratory syndrome coronavirus 2

<400> SEQUENCE: 20

Gln Pro Thr Glu Ser Ile Val Arg
1               5

<210> SEQ ID NO 21
<211> LENGTH: 7
<212> TYPE: PRT
<213> ORGANISM: Severe acute respiratory syndrome coronavirus 2

<400> SEQUENCE: 21

Pro Thr Glu Ser Ile Val Arg
1               5

<210> SEQ ID NO 22
<211> LENGTH: 6
<212> TYPE: PRT
<213> ORGANISM: Severe acute respiratory syndrome coronavirus 2

<400> SEQUENCE: 22

Thr Glu Ser Ile Val Arg
1               5

<210> SEQ ID NO 23
<211> LENGTH: 5
<212> TYPE: PRT
<213> ORGANISM: Severe acute respiratory syndrome coronavirus 2

<400> SEQUENCE: 23

Glu Ser Ile Val Arg
1               5

<210> SEQ ID NO 24
<211> LENGTH: 4
<212> TYPE: PRT
<213> ORGANISM: Severe acute respiratory syndrome coronavirus 2

<400> SEQUENCE: 24

Ser Ile Val Arg
1

<210> SEQ ID NO 25
<211> LENGTH: 9
<212> TYPE: PRT
<213> ORGANISM: Severe acute respiratory syndrome coronavirus 2

<400> SEQUENCE: 25

Gly Pro Lys Lys Ser Thr Asn Leu Val
1 5

<210> SEQ ID NO 26
<211> LENGTH: 8
<212> TYPE: PRT
<213> ORGANISM: Severe acute respiratory syndrome coronavirus 2

<400> SEQUENCE: 26

Gly Pro Lys Lys Ser Thr Asn Leu
1 5

<210> SEQ ID NO 27
<211> LENGTH: 7
<212> TYPE: PRT
<213> ORGANISM: Severe acute respiratory syndrome coronavirus 2

<400> SEQUENCE: 27

Gly Pro Lys Lys Ser Thr Asn
1 5

<210> SEQ ID NO 28
<211> LENGTH: 6
<212> TYPE: PRT
<213> ORGANISM: Severe acute respiratory syndrome coronavirus 2

<400> SEQUENCE: 28

Gly Pro Lys Lys Ser Thr
1 5

<210> SEQ ID NO 29
<211> LENGTH: 5
<212> TYPE: PRT
<213> ORGANISM: Severe acute respiratory syndrome coronavirus 2

<400> SEQUENCE: 29

Gly Pro Lys Lys Ser
1 5

<210> SEQ ID NO 30
<211> LENGTH: 4
<212> TYPE: PRT
<213> ORGANISM: Severe acute respiratory syndrome coronavirus 2

<400> SEQUENCE: 30

Gly Pro Lys Lys
1

<210> SEQ ID NO 31
<211> LENGTH: 9
<212> TYPE: PRT
<213> ORGANISM: Severe acute respiratory syndrome coronavirus 2

<400> SEQUENCE: 31

Lys Gly Ile Tyr Gln Thr Ser Asn Phe

-continued 1 5

<210> SEQ ID NO 32
<211> LENGTH: 8
<212> TYPE: PRT
<213> ORGANISM: Severe acute respiratory syndrome coronavirus 2

<400> SEQUENCE: 32

Gly Ile Tyr Gln Thr Ser Asn Phe
1 5

<210> SEQ ID NO 33
<211> LENGTH: 7
<212> TYPE: PRT
<213> ORGANISM: Severe acute respiratory syndrome coronavirus 2

<400> SEQUENCE: 33

Ile Tyr Gln Thr Ser Asn Phe
1 5

<210> SEQ ID NO 34
<211> LENGTH: 6
<212> TYPE: PRT
<213> ORGANISM: Severe acute respiratory syndrome coronavirus 2

<400> SEQUENCE: 34

Tyr Gln Thr Ser Asn Phe
1 5

<210> SEQ ID NO 35
<211> LENGTH: 5
<212> TYPE: PRT
<213> ORGANISM: Severe acute respiratory syndrome coronavirus 2

<400> SEQUENCE: 35

Gln Thr Ser Asn Phe
1 5

<210> SEQ ID NO 36
<211> LENGTH: 4
<212> TYPE: PRT
<213> ORGANISM: Severe acute respiratory syndrome coronavirus 2

<400> SEQUENCE: 36

Thr Ser Asn Phe
1

<210> SEQ ID NO 37
<211> LENGTH: 9
<212> TYPE: PRT
<213> ORGANISM: Severe acute respiratory syndrome coronavirus 2

<400> SEQUENCE: 37

Asn Lys Cys Val Asn Phe Asn Phe Asn
1 5

<210> SEQ ID NO 38
<211> LENGTH: 8
<212> TYPE: PRT
<213> ORGANISM: Severe acute respiratory syndrome coronavirus 2

<400> SEQUENCE: 38

Asn Lys Cys Val Asn Phe Asn Phe
1 5

-continued

```
<210> SEQ ID NO 39
<211> LENGTH: 7
<212> TYPE: PRT
<213> ORGANISM: Severe acute respiratory syndrome coronavirus 2

<400> SEQUENCE: 39

Asn Lys Cys Val Asn Phe Asn
1               5


<210> SEQ ID NO 40
<211> LENGTH: 5
<212> TYPE: PRT
<213> ORGANISM: Severe acute respiratory syndrome coronavirus 2

<400> SEQUENCE: 40

Asn Lys Cys Val Asn
1               5


<210> SEQ ID NO 41
<211> LENGTH: 4
<212> TYPE: PRT
<213> ORGANISM: Severe acute respiratory syndrome coronavirus 2

<400> SEQUENCE: 41

Asn Lys Cys Val
1


<210> SEQ ID NO 42
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 42

His His His His His His
1               5
```

SARS-CoV-2 SPIKE RECEPTOR BINDING DOMAIN AND COMPOSITIONS AND METHODS THEREOF

CROSS-REFERENCE TO RELATED APPLICATION

This application claims priority to U.S. Provisional Application No. 63/011,761 that was filed on Apr. 17, 2020. The entire content of the application referenced above is hereby incorporated by reference herein.

SEQUENCE LISTING

The instant application contains a Sequence Listing which has been submitted electronically in ASCII format and is hereby incorporated by reference in its entirety. Said ASCII copy, created on Oct. 25, 2022, is named 09531_514US1_SL.txt and is 33,716 bytes in size.

GOVERNMENT FUNDING

This invention was made with government support under A1089728 awarded by the National Institutes of Health. The government has certain rights in the invention.

BACKGROUND OF THE INVENTION

Coronaviruses, which cause disease in mammals and birds, are a group of enveloped viruses that have a positive-sense single-stranded RNA genome and a nucleocapsid of helical symmetry. Their genome encodes four major structural proteins: spike (S), membrane (M), envelope (E) and nucleocapsid (N). In humans, coronaviruses cause respiratory tract infections that can range from mild to lethal. Mild illnesses include some cases of the common cold, while more lethal varieties can cause COVID-19, SARS and MERS. SARS-coronavirus 2 (SARS-CoV-2) causes COVID-19, a disease that has spread rapidly and created a global health emergency. Due to the recent emergence of SARS-CoV-2, there are very few tools for either diagnostic tests or therapeutic interventions. A current barrier to creating tools is the lack of ability to produce high yields of viral proteins for testing. Thus, there is a need for new approaches for developing such tools, as well as COVID-19 specific diagnostic tests and therapeutic agents that prevent or ameliorate these infections.

SUMMARY OF THE INVENTION

Certain embodiments provide an isolated or purified polypeptide comprising a SARS-CoV-2 receptor binding domain (RBD) operably linked to a peptide tag (e.g., an affinity tag).

Certain embodiments provide an isolated or purified polypeptide comprising a SARS-CoV-2 receptor binding domain (RBD) linked directly or through a linker group to a peptide tag (e.g., an affinity tag), wherein the SARS-CoV-2 RBD is between about 197 to about 237 amino acids in length.

Certain embodiments provide an isolated or purified polypeptide comprising a SARS-CoV-2 receptor binding domain (RBD) linked directly or through a linker group to a peptide tag (e.g., an affinity tag), wherein the SARS-CoV-2 RBD is between about 197 to about 237 amino acids in length; and wherein the SARS-CoV-2 RBD comprises an amino acid sequence having at least 90% identity to a sequence corresponding to SEQ ID NO:5, or wherein the SARS-CoV-2 RBD comprises at least 90% identity to the sequence corresponding to SEQ ID NO:2.

Certain embodiments provide an isolated or purified polypeptide comprising a SARS-CoV-2 receptor binding domain (RBD) linked directly or through a linker group to a peptide tag (e.g., an affinity tag), wherein the SARS-CoV-2 RBD is between about 197 to about 237 amino acids in length; and wherein the SARS-CoV-2 RBD comprises an amino acid sequence having at least 90% identity to a sequence corresponding to SEQ ID NO:10.

Certain embodiments provide an isolated or purified polypeptide comprising a SARS-CoV-2 receptor binding domain (RBD) linked directly or through a linker group to a peptide tag (e.g., an affinity tag), wherein the SARS-CoV-2 RBD is between about 197 to about 237 amino acids in length; and wherein the SARS-CoV-2 RBD comprises an amino acid sequence having at least 90% identity to a sequence corresponding to SEQ ID NO:2.

Certain embodiments also provide a composition comprising a polypeptide as described herein and a carrier.

Certain embodiments provide an isolated polynucleotide comprising a nucleotide sequence encoding the polypeptide as described herein.

Certain embodiments provide an expression cassette comprising a promoter operably linked to the polynucleotide described herein.

Certain embodiments provide a vector comprising the polynucleotide as described herein or an expression cassette as described herein.

Certain embodiments provide a cell comprising a polynucleotide as described herein, an expression cassette as described herein or a vector as described herein.

Certain embodiments provide a method of making a cell as described herein, the method comprising transfecting or transducing the cell with a polynucleotide as described herein, an expression cassette as described herein or a vector as described herein.

Certain embodiments provide a method of producing a polypeptide, the method comprising transfecting or transducing a cell with a polynucleotide as described herein, an expression cassette as described herein or a vector as described herein.

Certain embodiments provide a method of producing a polypeptide, the method comprising culturing a cell as described herein under conditions appropriate for polypeptide expression.

Certain embodiments provide a polypeptide produced by a method as described herein.

The invention also provides processes and intermediates disclosed herein that are useful for preparing polypeptides and cells of the invention, as well as compositions described herein.

BRIEF DESCRIPTION OF THE FIGURES

FIG. 1A. Schematic of spike protein from SARS-CoV2 (top) and amino acid sequence (SEQ ID NO: 3) for a SARS-CoV2-RBD segment with a His8 tag (SEQ ID NO: 6) at the C-terminus (bottom). FIG. 1B. SARS-CoV-2 expression construct map. FIG. 1B discloses "8×His" as SEQ ID NO: 6.

FIG. 2A. Western blot. FIG. 2B SDS-PAGE gel stained by Coomassie Blue.

DETAILED DESCRIPTION

Figure 1A:
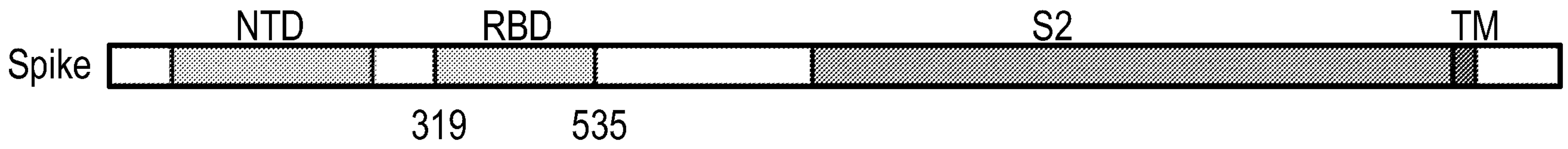
FIGS. 1A-1B.

Coronaviruses (CoV) are positive sense, single-stranded RNA viruses whose genome encodes 4 major structural proteins: spike (S), membrane (M), envelope (E), and nucleocapsid (N). The S protein mediates binding of the virus to the host cell receptor, and fusion between the two membranes allows for viral entry into the host cell. The S protein of SARS-CoV-2 consists of 2 subunits, S1 and S2. The S1 subunit binds to the host receptor through its receptor-binding domain (RBD), allowing for conformational changes and membrane fusion.

Described herein is the generation of genetically modified mammalian cells that can be used to produce a recombinant SARS-CoV-2 RBD polypeptide. Purified recombinant protein can be quickly obtained from these cells with a high yield and high purity (e.g., as compared to a transiently transfected cell). Additionally, the resulting protein is properly folded and biologically active (i.e., it binds to human angiotensin-converting enzyme 2 (ACE2)) (see, FIG. 3). Unlike protein produced in other cell systems, such as insect cells, the recombinant protein produced from a cell of the invention is also properly glycosylated, resulting in a more antigenic protein. In particular, the invention described herein provides a superior yield of high quality recombinant RBD protein, which is faithful to the SARS-CoV-2 RBD native folding/epitopes (e.g., a yield greater than 40 mg/liter cell culture). Additionally, this system may be readily scaled up for commercial uses. Accordingly, both the cells of the invention and the resulting SARS-CoV-2 RBD polypeptide are valuable tools for the development of COVID-19 diagnostic assays and therapeutic agents (e.g., vaccine compositions).

While not wishing to be bound by theory, it is believed that the design of the nucleic acid construct used in the genetically modified cells may contribute to many of these advantageous properties discussed above. In particular, construct variability has been shown to have a significant impact on protein expression levels and protein quality. As described herein, a certain fragment of the S1 subunit was selected for expression in these cells (e.g., SEQ ID NO:2) and was subsequently operably linked to a tPA signal peptide and an affinity tag.

Polypeptides

Accordingly, certain embodiments of the invention provide an isolated or substantially purified polypeptide comprising a SARS-CoV-2 receptor binding domain (RBD). In certain embodiments, the polypeptide is a recombinant polypeptide.

In certain embodiments, the SARS-CoV-2 RBD comprises an amino acid sequence having at least about 80% sequence identity to SEQ ID NO:2. In certain embodiments, the SARS-CoV-2 RBD comprises an amino acid sequence having at least about 81%, 82%, 83%, 84%, 85%, 86%, 87%, 88%, 89%, 90%, 91%, 92%, 93%, 94%, 95%, 96%, 97%, 98%, 99% or 100% identity to SEQ ID NO:2. In certain embodiments, the SARS-CoV-2 RBD comprises an amino acid sequence having at least about 85% sequence identity to SEQ ID NO:2. In certain embodiments, the SARS-CoV-2 RBD comprises an amino acid sequence having at least about 90% sequence identity to SEQ ID NO:2. In certain embodiments, the SARS-CoV-2 RBD comprises an amino acid sequence having at least about 95% sequence identity to SEQ ID NO:2. In certain embodiments, the SARS-CoV-2 RBD comprises an amino acid sequence having at least about 99% sequence identity to SEQ ID NO:2. In certain embodiments, the SARS-CoV-2 RBD comprises SEQ ID NO:2. In certain embodiments, the SARS-CoV-2 RBD consists of SEQ ID NO:2.

In certain embodiments, the SARS-CoV-2 RBD comprises an amino acid sequence having at least about 80% sequence identity to SEQ ID NO:5. In certain embodiments, the SARS-CoV-2 RBD comprises an amino acid sequence having at least about 81%, 82%, 83%, 84%, 85%, 86%, 87%, 88%, 89%, 90%, 91%, 92%, 93%, 94%, 95%, 96%, 97%, 98%, 99% or 100% identity to SEQ ID NO:5. In certain embodiments, the SARS-CoV-2 RBD comprises an amino acid sequence having at least about 85% sequence identity to SEQ ID NO:5. In certain embodiments, the SARS-CoV-2 RBD comprises an amino acid sequence having at least about 90% sequence identity to SEQ ID NO:5. In certain embodiments, the SARS-CoV-2 RBD comprises an amino acid sequence having at least about 95% sequence identity to SEQ ID NO:5. In certain embodiments, the SARS-CoV-2 RBD comprises an amino acid sequence having at least about 99% sequence identity to SEQ ID NO:5. In certain embodiments, the SARS-CoV-2 RBD comprises SEQ ID NO:5. In certain embodiments, the SARS-CoV-2 RBD consists of SEQ ID NO:5.

In certain embodiments, the SARS-CoV-2 RBD amino acid sequence is between about 197 to about 237 amino acids in length. In certain embodiments, the SARS-CoV-2 RBD amino acid sequence is between about 207 to about 227 amino acids in length. In certain embodiments, the SARS-CoV-2 RBD amino acid sequence is between about 210 to about 225 amino acids in length. In certain embodiments, the SARS-CoV-2 RBD amino acid sequence is between about 210 to about 222 amino acids in length. In certain embodiments, the SARS-CoV-2 RBD amino acid sequence is between about 211 to about 222 amino acids in length. In certain embodiments, the SARS-CoV-2 RBD amino acid sequence is between about 212 to about 222 amino acids in length. In certain embodiments, the SARS-CoV-2 RBD amino acid sequence is between about 213 to about 221 amino acids in length. In certain embodiments, the SARS-CoV-2 RBD amino acid sequence is between about 215 to about 219 amino acids in length. In certain embodiments, the SARS-CoV-2 RBD amino acid sequence is between about 216 to about 218 amino acids in length. In certain embodiments, the SARS-CoV-2 RBD amino acid sequence is 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236 or 237 amino acids in length. In certain embodiments, the SARS-CoV-2 RBD amino acid sequence is 217 amino acids in length.

In certain embodiments, 1, 2, 3, 4, 5, 6, 7, 8, 9, or 10 amino acids located at positions 1-10 in reference to SEQ ID NO:5 are not comprised within the SARS-CoV-2 RBD amino acid sequence. In certain embodiments, 1, 2, 3, 4, 5, 6, 7, 8, 9, or 10 amino acids located at positions 228-237 in reference to SEQ ID NO:5 are not comprised within the SARS-CoV-2 RBD amino acid sequence.

In certain embodiments, the SARS-CoV-2 RBD comprises an amino acid sequence having at least 90% identity to the sequence corresponding to SEQ ID NO:5, wherein from 1 to 10 (e.g., consecutive) amino acids located at positions 1-10 in reference to the sequence corresponding to SEQ ID NO:5 are not comprised within the SARS-CoV-2 RBD amino acid sequence. In certain embodiments, from 1 to 9 (e.g., consecutive) amino acids located at positions 1-9;

or from 1 to 8 (e.g., consecutive) amino acids located at positions 1-8; or from 1 to 7 (e.g., consecutive) amino acids located at positions 1-7; or from 1 to 6 (e.g., consecutive) amino acids located at positions 1-6; or from 1 to 5 (e.g., consecutive) amino acids located at positions 1-5; or from 1 to 4 (e.g., consecutive) amino acids located at positions 1-4; or from 1 to 3 (e.g., consecutive) amino acids located at positions 1-3; or from 1 to 2 (e.g., consecutive) amino acids located at positions 1-2; or 1 amino acid located at position 1, in reference to the sequence corresponding to SEQ ID NO:5 are not comprised within the SARS-CoV-2 RBD amino acid sequence.

In certain embodiments, the SARS-CoV-2 RBD comprises an amino acid sequence having at least 90% identity to a sequence corresponding to SEQ ID NO:5, and wherein from 1 to 10 (e.g., consecutive) amino acids located at positions 228-237 in reference to the sequence corresponding to SEQ ID NO:5 are not comprised within the SARS-CoV-2 RBD amino acid sequence. In certain embodiments, from 1 to 9 (e.g., consecutive) amino acids located at positions 229-237; or from 1 to 8 (e.g., consecutive) amino acids located at positions 230-237; or from 1 to 7 (e.g., consecutive) amino acids located at positions 231-237; or from 1 to 6 (e.g., consecutive) amino acids located at positions 232-237; or from 1 to 5 (e.g., consecutive) amino acids located at positions 233-237; or from 1 to 4 (e.g., consecutive) amino acids located at positions 234-237; or from 1 to 3 (e.g., consecutive) amino acids located at positions 235-237; or from 1 to 2 (e.g., consecutive) amino acids located at positions 236-237; or 1 amino acid located at position 237, in reference to the sequence corresponding to SEQ ID NO:5 are not comprised within the SARS-CoV-2 RBD amino acid sequence.

In certain embodiments, the SARS-CoV-2 RBD comprises an amino acid sequence having at least 90% identity to the sequence corresponding to SEQ ID NO:5, wherein from 1 to 10 amino acids located at positions 1-10 in reference to the sequence corresponding to SEQ ID NO:5 are not comprised within the SARS-CoV-2 RBD amino acid sequence (or a smaller range as recited above), and wherein from 1 to 10 amino acids located at positions 228-237 in reference to the sequence corresponding to SEQ ID NO:5 are not comprised within the SARS-CoV-2 RBD amino acid sequence (or a smaller range as recited above).

In certain embodiments, the amino acid at the C-terminus of SARS-CoV-2 RBD is lysine (K). In certain embodiments, the last seven amino acids at the C-terminus of the SARS-CoV-2 RBD is KSTNLVK (SEQ ID NO: 15). In certain embodiments, the last six amino acids at the C-terminal of the SARS-CoV-2 RBD is STNLVK (SEQ ID NO: 16). For example, in certain embodiments, the SARS-CoV-2 RBD amino acid sequence ends with a segment of STNLVK (SEQ ID NO: 16) at the C-terminus.

In certain embodiments, the last seven amino acids at the C-terminus of the SARS-CoV-2 RBD is not NKCVNFS (SEQ ID NO: 17). In certain embodiments, the last six amino acids at the C-terminus of the SARS-CoV-2 RBD is not NKCVNF (SEQ ID NO: 18). For example, in certain embodiments, the SARS-CoV-2 RBD does not end with a segment of NKCVNFS (SEQ ID NO: 17) or NKCVNF (SEQ ID NO: 18) at the C-terminus.

In certain embodiments, the last seven amino acids at the C-terminus of the SARS-CoV-2 RBD is not NKCVNFS. In certain embodiments, the last six amino acids at the C-terminus of the SARS-CoV-2 RBD is not NKCVNF. For example, in certain embodiments, the SARS-CoV-2 RBD does not end with a segment of NKCVNFS or NKCVNF at the C-terminus.

In certain embodiments, 1, 2, 3, 4, 5, 6, 7, 8, 9 or 10 amino acids located at positions 1-10 in reference to SEQ ID NO:2 are not comprised within the SARS-CoV-2 RBD amino acid sequence. In certain embodiments, 1, 2, 3, 4, 5, 6, 7, 8, 9 or 10 amino acids located at positions 208-217 in reference to SEQ ID NO:2 are not comprised within the SARS-CoV-2 RBD amino acid sequence.

In certain embodiments, the SARS-CoV-2 RBD comprises an amino acid sequence having at least 90% identity to the sequence corresponding to SEQ ID NO:2, wherein from 1 to 10 amino acids located at positions 1-10 in reference to the sequence corresponding to SEQ ID NO:2 are not comprised within the SARS-CoV-2 RBD amino acid sequence. In certain embodiments, from 1 to 9 (e.g., consecutive) amino acids located at positions 1-9; or from 1 to 8 (e.g., consecutive) amino acids located at positions 1-8; or from 1 to 7 (e.g., consecutive) amino acids located at positions 1-7; or from 1 to 6 (e.g., consecutive) amino acids located at positions 1-6; or from 1 to 5 (e.g., consecutive) amino acids located at positions 1-5; or from 1 to 4 (e.g., consecutive) amino acids located at positions 1-4; or from 1 to 3 (e.g., consecutive) amino acids located at positions 1-3; or from 1 to 2 (e.g., consecutive) amino acids located at positions 1-2; or 1 amino acid located at position 1, in reference to the sequence corresponding to SEQ ID NO:2 are not comprised within the SARS-CoV-2 RBD amino acid sequence.

In certain embodiments, the SARS-CoV-2 RBD comprises an amino acid sequence having at least 90% identity to the sequence corresponding to SEQ ID NO:2, wherein from 1 to 10 (e.g., consecutive) amino acids located at positions 208-217 in reference to the sequence corresponding to SEQ ID NO:2 are not comprised within the SARS-CoV-2 RBD amino acid sequence. In certain embodiments, from 1 to 9 (e.g., consecutive) amino acids located at positions 209-217; or from 1 to 8 (e.g., consecutive) amino acids located at positions 210-217; or from 1 to 7 (e.g., consecutive) amino acids located at positions 211-217; or from 1 to 6 (e.g., consecutive) amino acids located at positions 212-217; or from 1 to 5 (e.g., consecutive) amino acids located at positions 213-217; or from 1 to 4 (e.g., consecutive) amino acids located at positions 214-217; or from 1 to 3 (e.g., consecutive) amino acids located at positions 215-217; or from 1 to 2 (e.g., consecutive) amino acids located at positions 216-217; or 1 amino acid located at position 217, in reference to the sequence corresponding to SEQ ID NO:2 are not comprised within the SARS-CoV-2 RBD amino acid sequence.

In certain embodiments, the SARS-CoV-2 RBD comprises an amino acid sequence having at least 90% identity to the sequence of SEQ ID NO:2, and wherein from 1 to 10 amino acids located at positions 1-10 in reference to the sequence corresponding to SEQ ID NO:2 are not comprised within the SARS-CoV-2 RBD amino acid sequence (or a smaller range as recited above), and wherein from 1 to 10 amino acids located at positions 208-217 in reference to the sequence corresponding to SEQ ID NO:2 are not comprised within the SARS-CoV-2 RBD amino acid sequence (or a smaller range as recited above).

In certain embodiments, the SARS-COV-2 RBD comprises an amino acid sequence having at least 90% identity to a sequence corresponding to SEQ ID NO:10. In certain embodiments, the SARS-COV-2 RBD further comprises from 1 to 10 (e.g., consecutive) amino acids provided in a sequence corresponding to SEQ ID NO:11. For example, in certain embodiments, the SARS-COV-2 RBD the amino-terminus comprises RVQPTESIVR (SEQ ID NO: 11), VQP-TESIVR (SEQ ID NO: 19), QPTESIVR (SEQ ID NO: 20), PTESIVR (SEQ ID NO: 21), TESIVR (SEQ ID NO: 22), ESIVR (SEQ ID NO: 23), SIVR (SEQ ID NO: 24), IVR, VR, or R. In certain embodiments, the SARS-COV-2 RBD further comprises from 1 to 10 amino acids provided in a sequence corresponding to SEQ ID NO:12. In certain embodiments, the SARS-COV-2 RBD carboxy-terminus comprises GPKKSTNLVK (SEQ ID NO: 12), GPKK-STNLV (SEQ ID NO: 25), GPKKSTNL (SEQ ID NO: 26), GPKKSTN (SEQ ID NO: 27), GPKKST (SEQ ID NO: 28), GPKKS (SEQ ID NO: 29), GPKK (SEQ ID NO: 30), GPK, GP, or G. In certain embodiments, the SARS-COV-2 RBD further comprises 1 to 10 amino acids provided in a sequence corresponding to SEQ ID NO: 11, and further comprises from 1 to 10 amino acids provided in a sequence corresponding to SEQ ID NO:12. In certain embodiments, the SARS-COV-2 RBD the amino-terminus comprises RVQPTESIVR (SEQ ID NO: 11), VQPTESIVR (SEQ ID NO: 19), QPTESIVR (SEQ ID NO: 20), PTESIVR (SEQ ID NO: 21), TESIVR (SEQ ID NO: 22), ESIVR (SEQ ID NO: 23), SIVR (SEQ ID NO: 24), IVR, VR, or R and the carboxy-terminus comprises GPKKSTNLV (SEQ ID NO: 25), GPKKSTNL (SEQ ID NO: 26), GPKKSTN (SEQ ID NO: 27), GPKKST (SEQ ID NO: 28), GPKKS (SEQ ID NO: 29), GPKK (SEQ ID NO: 30), GPK, GP, or G.

In certain embodiments, the SARS-COV-2 RBD comprises an amino acid sequence having at least 90% identity to a sequence corresponding to SEQ ID NO:2. In certain embodiments, the SARS-COV-2 RBD further comprises from 1 to 10 amino acids provided in the sequence corresponding to SEQ ID NO:13. For example, in certain embodiments, the SARS-COV-2 RBD the amino-terminus comprises EKGIYQTSNF (SEQ ID NO: 13), KGIYQTSNF (SEQ ID NO: 31), GIYQTSNF (SEQ ID NO: 32), IYQTSNF (SEQ ID NO: 33), YQTSNF (SEQ ID NO: 34), QTSNF (SEQ ID NO: 35), TSNF (SEQ ID NO: 36), SNF, NF or F. In certain embodiments, the SARS-COV-2 RBD further comprises from 1 to 10 amino acids provided in the sequence corresponding to SEQ ID NO:14. In certain embodiments, the SARS-CoV-2 RBD carboxy-terminus comprises NKCVNFNFNG (SEQ ID NO: 14), NKCVNFNFN (SEQ ID NO: 37), NKCVNFNF (SEQ ID NO: 38), NKCVNFN (SEQ ID NO: 39), NKCVNF (SEQ ID NO: 18), NKCVN (SEQ ID NO: 40), NKCV (SEQ ID NO: 41), NKC, NK, or N. In certain embodiments, the SARS-COV-2 RBD further comprises 1 to 10 amino acids provided in the sequence corresponding to SEQ ID NO:13, and further comprises from 1 to 10 amino acids provided in the sequence corresponding to SEQ ID NO:14. In certain embodiments, the SARS-CoV-2 RBD the amino-terminus comprises EKGIYQTSNF (SEQ ID NO: 13), KGIYQTSNF (SEQ ID NO: 31), GIYQTSNF (SEQ ID NO: 32), IYQTSNF (SEQ ID NO: 33), YQTSNF (SEQ ID NO: 34), QTSNF (SEQ ID NO: 35), TSNF (SEQ ID NO: 36), SNF, NF or F, and the carboxy-terminus comprises NKCVNFNFN (SEQ ID NO: 37), NKCVNFNF (SEQ ID NO: 38), NKCVNFN (SEQ ID NO: 39), NKCVNF (SEQ ID NO: 18), NKCVN (SEQ ID NO: 40), NKCV (SEQ ID NO: 41), NKC, NK, or N.

In certain embodiments, the polypeptide further comprises one or more detectable markers, such as a protein or peptide tag or a fluorescent tag. In certain embodiments, the polypeptide comprises one or more peptides or proteins that are useful for purification (e.g., an epitope tag). In some embodiments, the detectable marker and/or peptide/protein for purification is attached to the N-terminal end and/or the C-terminal end of the RBD amino acid sequence.

In certain embodiments, the polypeptide comprises an amino acid sequence encoding a peptide tag. In certain embodiments, the peptide tag is an affinity tag. In certain embodiments, the tag is a poly(His) tag, FLAG, 3×FLAG, c-Myc, Fc tag, or a hemagglutinin tag (e.g. HA). In certain embodiments, the tag is a poly(His) tag. In certain embodiments, the peptide tag is a 6×His tag (SEQ ID NO: 42). In certain embodiments, the tag is an 8×His tag (SEQ ID NO: 6)

In certain embodiments, the peptide tag is operably linked to the N-terminus of the RBD amino acid sequence. In certain embodiments, the peptide tag is operably linked to the C-terminus of the RBD amino acid sequence.

In certain embodiments, the peptide tag is directly linked to the RBD amino acid sequence. In certain embodiments, the peptide tag is linked to the RBD amino acid sequence through a linker group. In certain embodiments, the linker group is a peptide linker, such as a GS rich amino acid sequence. In certain embodiments, the linker group is a di-peptide, such as GS.

In certain embodiments, the linker group is about 1 to about 30 amino acids in length. In certain embodiments, the linker group is about 1 to about 25 amino acids in length. In certain embodiments, the linker group is about 1 to about 20 amino acids in length. In certain embodiments, the linker group is about 1 to about 15 amino acids in length. In certain embodiments, the linker group is about 1 to about 12 amino acids in length. In certain embodiments, the linker group is about 1 to about 10 amino acids in length. In certain embodiments, the linker group is about 1 to about 9 amino acids in length. In certain embodiments, the linker group is about 1 to about 8 amino acids in length. In certain embodiments, the linker group is about 1 to about 7 amino acids in length. In certain embodiments, the linker group is about 1 to about 6 amino acids in length. In certain embodiments, the linker group is about 1 to about 5 amino acids in length. In certain embodiments, the linker group is about 1 to about 4 amino acids in length. In certain embodiments, the linker group is about 1 to about 3 amino acids in length. In certain embodiments, the linker group is about 2 amino acids in length.

In certain embodiments, the polypeptide comprises an amino acid sequence having at least about 80% identity to SEQ ID NO:3. In certain embodiments, the polypeptide comprises an amino acid sequence having at least about 81%, 82%, 83%, 84%, 85%, 86%, 87%, 88%, 89%, 90%, 91%, 92%, 93%, 94%, 95%, 96%, 97%, 98%, 99% or 100% identity to SEQ ID NO:3. In certain embodiments, the polypeptide comprises an amino acid sequence having at least about 85% sequence identity to SEQ ID NO:3. In certain embodiments, the polypeptide comprises an amino acid sequence having at least about 90% sequence identity to SEQ ID NO:3. In certain embodiments, the polypeptide comprises an amino acid sequence having at least about 95% sequence identity to SEQ ID NO:3. In certain embodiments, the polypeptide comprises an amino acid sequence having at least about 99% sequence identity to SEQ ID NO:3. In certain embodiments, the polypeptide comprises SEQ ID NO:3. In certain embodiments, the polypeptide consists of SEQ ID NO:3.

In certain embodiments, the polypeptide further comprises a signal peptide. In certain embodiments, the signal peptide is tPA signal peptide (e.g., SEQ ID NO: 7). In certain embodiments, the signal peptide is cleaved from the polypeptide prior to secretion.

In certain embodiments, the signal peptide is operably linked to the N-terminus of the RBD amino acid sequence. In certain embodiments, the signal peptide is operably linked to the C-terminus of the RBD amino acid sequence.

In certain embodiments, the signal peptide is directly linked to the RBD amino acid sequence. In certain embodiments, the signal peptide is linked to the RBD amino acid sequence through a linker group. In certain embodiments, the linker group is a peptide linker.

In certain embodiments, the polypeptide comprises an amino acid sequence having at least about 80% identity to SEQ ID NO:4. In certain embodiments, the polypeptide comprises an amino acid sequence having at least about 81%, 82%, 83%, 84%, 85%, 86%, 87%, 88%, 89%, 90%, 91%, 92%, 93%, 94%, 95%, 96%, 97%, 98%, 99% or 100% identity to SEQ ID NO:4. In certain embodiments, the polypeptide comprises an amino acid sequence having at least about 85% sequence identity to SEQ ID NO:4. In certain embodiments, the polypeptide comprises an amino acid sequence having at least about 90% sequence identity to SEQ ID NO:4. In certain embodiments, the polypeptide comprises an amino acid sequence having at least about 95% sequence identity to SEQ ID NO:4. In certain embodiments, the polypeptide comprises an amino acid sequence having at least about 99% sequence identity to SEQ ID NO:4. In certain embodiments, the polypeptide comprises SEQ ID NO:4. In certain embodiments, the polypeptide consists of SEQ ID NO:4.

In certain embodiments, the polypeptide is between about 197 to about 1,000 amino acids in length. In certain embodiments, the polypeptide is between about 197 to about 1,000 amino acids in length. In certain embodiments, the polypeptide is between about 197 to about 750 amino acids in length. In certain embodiments, the polypeptide is between about 197 to about 500 amino acids in length. In certain embodiments, the polypeptide is between about 197 to about 400 amino acids in length. In certain embodiments, the polypeptide is between about 197 to about 350 amino acids in length. In certain embodiments, the polypeptide is between about 197 to about 300 amino acids in length. In certain embodiments, the polypeptide is between about 197 to about 275 amino acids in length. In certain embodiments, the polypeptide is between about 197 to about 270 amino acids in length. In certain embodiments, the polypeptide is between about 207 to about 270 amino acids in length. In certain embodiments, the polypeptide is between about 207 to about 250 amino acids in length. In certain embodiments, the polypeptide is between about 215 and about 219 amino acids in length. In certain embodiments, the polypeptide is about 217 amino acids in length. In certain embodiments, the polypeptide is between about 225 and about 229 amino acids in length. In certain embodiments, the polypeptide is about 227 amino acids in length. In certain embodiments, the polypeptide is between about 248 and about 252 amino acids in length. In certain embodiments, the polypeptide is about 250 amino acids in length.

In certain embodiments, the polypeptide is at least about 200 amino acids in length. In certain embodiments, the polypeptide is at least about 215 amino acids in length. In certain embodiments, the polypeptide is at least about 217 amino acids in length. In certain embodiments, the polypeptide is at least about 225 amino acids in length. In certain embodiments, the polypeptide is at least about 227 amino acids in length. In certain embodiments, the polypeptide is at least about 245 amino acids in length. In certain embodiments, the polypeptide is at least about 250 amino acids in length.

In certain embodiments, the polypeptide comprises the spike RBD but does not comprise other spike protein domains. For example, in certain embodiments the polypeptide does not comprise an N-terminal domain, an S2 domain, a transmembrane domain, and/or an intracellular domain. In certain embodiments the polypeptide does not comprise the following spike protein domains: an N-terminal domain, an S2 domain, a transmembrane domain, and an intracellular domain. In certain embodiments, the polypeptide is a SAR-COV-2 RBD polypeptide (e.g., an RBD polypeptide described herein) operably linked to a peptide tag (e.g., an affinity tag), and optionally, wherein a signal peptide sequence is further operably linked to the SARS-CoV-2 RBD. In certain embodiments, the polypeptide consists of a SARS-CoV-2 RBD (e.g., an RBD polypeptide described herein) linked directly or through a linker group to a peptide tag (e.g., an affinity tag), and optionally, wherein a signal peptide sequence is further operably linked (e.g., directly linked or through a linker group) to the SARS-CoV-2 RBD.

In certain embodiments, the polypeptide is capable of binding to angiotensin-converting enzyme 2 (ACE2) (e.g., with high affinity). In certain embodiments, ACE2 is human ACE2.

Certain embodiments of the invention provide a polypeptide as described herein.

Certain embodiments of the invention provide a polypeptide produced using a method described herein.

Certain embodiments of the invention provide a polypeptide produced from a cell described herein (e.g., a stably transfected mammalian cell).

Nucleic Acids, Expression Cassettes and Vectors

In some embodiments, the polypeptides described herein are prepared using recombinant methods. Accordingly, certain embodiments provide polynucleotides (e.g., isolated polynucleotides) comprising a nucleic acid sequence encoding any of the polypeptides described herein. The polynucleotides may be single-stranded or double-stranded. In some embodiments, the polynucleotide is DNA. In some embodiments, the polynucleotide is cDNA. In some embodiments, the polynucleotide is RNA. In some embodiments, the polynucleotide comprises a nucleic acid sequence that has at least about 90% (e.g., at least about 90%, 91%, 92%, 93%, 94%, 95%, 96%, 97%, 98%, 99% or 100%) sequence identity to SEQ ID NO:1.

In certain embodiments, the nucleic acid further comprises a promoter.

Certain embodiments of the invention provide an expression cassette comprising a nucleic acid sequence described herein and a promoter operably linked to the nucleic acid.

In certain embodiments, the promoter is a regulatable promoter. In certain embodiments, the promoter is a constitutive promoter.

In certain embodiments, the expression cassette further comprises an expression control sequence (e.g., an enhancer) operably linked to the nucleic acid sequence. Expression control sequences and techniques for operably linking sequences together are well known in the art.

Nucleic acids/expression cassettes encoding a polypeptide described herein can be engineered into a vector using standard ligation techniques, such as those described in Sambrook and Russell, Molecular Cloning: A Laboratory Manual, Cold Spring Harbor Laboratory Press Cold Spring Harbor, NY (2001). For example, ligations can be accomplished in 20 mM Tris-Cl pH 7.5, 10 mM MgCl2, 10 mM DTT, 33 μg/ml BSA, 10 mM-50 mM NaCl, and either 40 μM ATP, 0.01-0.02 (Weiss) units T4 DNA ligase at 0° C. (for "sticky end" ligation) or 1 mM ATP, 0.3-0.6 (Weiss) units T4 DNA ligase at 14° C. (for "blunt end" ligation). Intermolecular "sticky end" ligations are usually performed at 30-100 μg/ml total DNA concentrations (5-100 nM total end concentration).

Accordingly, certain embodiments of the invention provide a vector comprising an expression cassette described herein. In particular, certain embodiments provide a vector comprising an expression cassette comprising a promoter operably linked to a nucleic acid sequence encoding a polypeptide of the invention (e.g., SEQ ID NO:3 or 4).

Non-limiting examples of vectors include plasmids and viral expression systems, such as a lentiviral, adenoviral, and adeno-associated virus (AAV) expression systems. Further non-limiting examples mammalian expression vectors include the pRc/CMV, pSV2gpt, pSV2neo, pcDNA3, pcDNAI/amp, pcDNAI/neo, pSV2-dhfr, pMSG, pSVT7, pTk2, pRSVneo, pko-neo, and pHyg-derived vectors. In certain embodiments, the vector is a lentivirus vector. In certain embodiments, the vector is a vector described herein.

Cells

Certain embodiments of the invention provide a cell comprising a polypeptide described herein, a nucleic acid described herein, an expression cassette described herein or a vector described herein.

In certain embodiments, the cell is a mammalian cell.

In certain embodiments, the cell is a human mammalian cell. In certain embodiments, the cell is a human embryonic kidney (HEK) 293 cell. In certain embodiments, the cell is a 293F cell. In certain embodiments, the cell is a 293T cell. In certain embodiments, the cell is a human embryonic retinal (PER.C6) cell. In certain embodiments, the cell is a HT-1080 cell. In certain embodiments, the cell is a Huh-7 cell.

In certain embodiments, the cell is a non-human mammalian cell. In certain embodiments, the cell is a Monkey kidney epithelial (Vero) cell. In certain embodiments, the cell is a Chinese Hamster Ovary (CHO) cell. In certain embodiments, the cell is a baby hamster kidney (BHK) cell.

In certain embodiments, the cell is a non-mammalian cell. In certain embodiments, the cell is an insect cell. In certain embodiments, the cell is a yeast cell. In certain embodiments, the cell is a bacteria cell.

Certain embodiments provide a cell produced using a method described herein.

In certain embodiments, a cell described herein is capable of producing a high yield of a polypeptide of the invention. For example, in certain embodiments, the cell is capable of producing at least about 30 mg/liter cell culture of the polypeptide. In certain embodiments, the cell is capable of producing at least about 35 mg/liter cell culture of the polypeptide. In certain embodiments, the cell is capable of producing at least about 40 mg/liter cell culture of the polypeptide. In certain embodiments, the cell is capable of producing at least about 45 mg/liter cell culture of the polypeptide. In certain embodiments, the cell is capable of producing at least about 50 mg/liter cell culture of the polypeptide. In certain embodiments, the cell is capable of producing at least about 55 mg/liter cell culture of the polypeptide. In certain embodiments, the cell is capable of producing at least about 60 mg/liter cell culture of the polypeptide. In certain embodiments, the cell is capable of producing at least about 65 mg/liter cell culture of the polypeptide. In certain embodiments, the cell is capable of producing at least about 70 mg/liter cell culture of the polypeptide. In certain embodiments, the cell is capable of producing about 30 mg/liter cell culture to about 70 mg/liter cell culture of the polypeptide. In certain embodiments, the cell is capable of producing about 35 mg/liter cell culture to about 65 mg/liter cell culture of the polypeptide. In certain embodiments, the cell is capable of producing about 40 mg/liter cell culture to about 60 mg/liter cell culture of the polypeptide.

A Polypeptide Immobilized on a Substrate

In certain embodiments, a polypeptide described herein is immobilized (e.g., covalently or non-covalently) on a substrate. In certain embodiments, the substrate is a solid substrate. In certain embodiments, a polypeptide described herein is coated on a substrate via passive adsorption. In certain embodiments, a polypeptide described herein is immobilized on a substrate via chemical conjugation or complexation. In certain embodiments, a polypeptide described herein is immobilized on a substrate via a capture antibody (e.g., an anti-His tag antibody).

In certain embodiments, the substrate is an ELISA plate (e.g., a polystyrene plate). In certain embodiments, the substrate is a particle (e.g., a nanoparticle or microparticle). In certain embodiments, the particle is a magnetic particle (e.g., a paramagnetic nanoparticle or microparticle). In certain embodiments, the substrate is a surface plasmon resonance (SPR) sensor chip.

In certain embodiments, the substrate is a matrix. In certain embodiments, the substrate is a matrix (e.g., sugar- or acrylamide-based polymer resin and/or gel) in an affinity column for isolating or purifying a SARS-Cov-2 RBD binder agent (e.g., antibody). In certain embodiments, the substrate is a porous matrix. In certain embodiments, the matrix is agarose, cellulose, dextran, polyacrylamide, latex or controlled pore glass. In certain embodiments, the polypeptide described herein is immobilized onto a matrix (e.g., for affinity column).

Compositions

Certain embodiments of the invention provide a composition comprising a polypeptide described herein and a carrier.

In certain embodiments, a polypeptide described herein is formulated for use in a diagnostic assay. In certain embodiments, the polypeptide is operably linked to a solid substrate or support, as described herein.

In certain embodiments, the composition is a pharmaceutical composition comprising a pharmaceutically acceptable carrier. In certain embodiments, the composition is a vaccine composition described herein.

Certain embodiments of the invention provide a lyophilized composition comprising the polypeptide or a nucleic acid sequence described herein.

In certain embodiments, the lyophilized composition further comprises one or more excipients selected from the group consisting of a cryo-lyoprotectant (e.g., trehalose, sucrose) and a bulking agent (e.g., mannitol, glycine).

Vaccines of the Invention

As described herein, the present invention also provides vaccine compositions, and methods of vaccination, effective to immunize a susceptible animal (e.g., a mammal, such as a human) against a SARS-CoV-2 infection.

Certain embodiments of the invention provide a vaccine composition comprising a polypeptide described herein and a pharmaceutically acceptable carrier.

Certain embodiments of the invention also provide a vaccine composition comprising an expression cassette comprising a promoter and a nucleic acid sequence encoding a polypeptide described herein (e.g., a polypeptide comprising a SARS-CoV-2 RBD) and a pharmaceutically acceptable carrier. In certain embodiments, the nucleic acid sequence is an RNA sequence. In certain embodiments, the nucleic acid sequence is a DNA sequence. In certain embodiments, the expression cassette is packaged within a lentivirus or an adenovirus.

In certain embodiments, the vaccine composition is a liquid formulation, a lyophilized formulation or an emulsion formulation.

In certain embodiments, the vaccine composition further comprises an adjuvant.

The term "adjuvant" as used herein refers to non-specific stimulators of the immune response or substances that allow generation of a depot in the host, which when combined with the vaccine and pharmaceutical composition, respectively, of the present invention may provide for an even more enhanced immune response. Vaccines commonly contain two components:

antigen and adjuvant. The antigen is the molecular structure encoded by the pathogen against which the immune response is directed. To activate an antigen-specific immune response, the antigen must be presented in the appropriate immunostimulatory microenvironment. In certain embodiments, adjuvants establish such microenvironments by stimulating the production of immune-activating molecules such as proinflammatory cytokines. Vaccine efficacy depends on the types of antigen and adjuvant, and how they are administered.

Immunogenic compositions as described herein also comprise, in certain embodiments, one or more adjuvants. An adjuvant is a substance that enhances the immune response when administered together with an immunogen or antigen. A number of cytokines or lymphokines have been shown to have immune modulating activity, and thus are useful as adjuvants, including, but not limited to, the interleukins 1-α, 1-β, 2, 4, 5, 6, 7, 8 and 10, 12 (see, e.g., U.S. Pat. No. 5,723,127), 13, 14, 15, 16, 17 and 18 (and its mutant forms); the interferons-α, β and γ; granulocyte-macrophage colony stimulating factor (GM-CSF) (see, e.g., U.S. Pat. No. 5,078,996 and ATCC Accession Number 39900); macrophage colony stimulating factor (M-CSF); granulocyte colony stimulating factor (G-CSF); and the tumor necrosis factors α and β. Still other adjuvants that are useful with the immunogenic compositions described herein include chemokines, including without limitation, MCP-1, MIP-1α, MIP-1β, and RANTES; adhesion molecules, such as a selectin, e.g., L-selectin, P-selectin and E-selectin; mucin-like molecules, e.g., CD34, GlyCAM-1 and MadCAM-1; a member of the integrin family such as LFA-1, VLA-1, Mac-1 and p150.95; a member of the immunoglobulin superfamily such as PECAM, ICAMs, e.g., ICAM-1, ICAM-2 and ICAM-3, CD2 and LFA-3; co-stimulatory molecules such as CD40 and CD40L; growth factors including vascular growth factor, nerve growth factor, fibroblast growth factor, epidermal growth factor, B7.2, PDGF, BL-1, and vascular endothelial growth factor; receptor molecules including Fas, TNF receptor, Flt, Apo-1, p55, WSL-1, DR3, TRAMP, Apo-3, AIR, LARD, NGRF, DR4, DR5, KILLER, TRAIL-R2, TRICK2, and DR6; and Caspase (ICE).

Still other adjuvants include muramyl peptides, such as N-acetyl-muramyl-L-threonyl-D-isoglutamine (thr-MDP), N-acetyl-normuramyl-L-alanine-2-(1'-2' dipalmitoyl-sn-glycero hydroxyphosphoryloxy)-ethylamine (MTP-PE); oil-in-water emulsions, such as MF59 (U.S. Pat. No. 6,299,884) (containing 5% Squalene, 0.5% Tween 80, and 0.5% Span 85 (optionally containing various amounts of MTP-PE) formulated into submicron particles using a microfluidizer such as Model 110Y microfluidizer (Microfluidics, Newton, MA)), and SAF (containing 10% Squalene, 0.4% Tween 80, 5% pluronic-blocked polymer L121, and thr-MDP, either microfluidized into a submicron emulsion or vortexed to generate a larger particle size emulsion); aluminum salts (alum), such as aluminum hydroxide, aluminum phosphate, aluminum sulfate; Amphigen; Avridine; L121/squalene; D-lactide-polylactide/glycoside; pluronic polyols; killed Bordetella; saponins, such as Stimulon™ QS-21 (Antigenics, Framingham, MA.), described in U.S. Pat. No. 5,057,540, ISCOMATRIX (CSL Limited, Parkville, Australia), described in U.S. Pat. No. 5,254,339, and immunostimulating complexes (ISCOMS); Mycobacterium tuberculosis; bacterial lipopolysaccharides; synthetic polynucleotides such as oligonucleotides containing a CpG motif (e.g., U.S. Pat. No. 6,207,646); IC-31 (Intercell AG, Vienna, Austria), described in European Patent Nos. 1,296,713 and 1,326,634; a pertussis toxin (PT) or mutant thereof, a cholera toxin or mutant thereof (e.g., U.S. Pat. Nos. 7,285,281, 7,332,174, 7,361,355 and 7,384,640); or an *E. coli* heat-labile toxin (LT) or mutant thereof, particularly LT-K63, LT-R72 (e.g., U.S. Pat. Nos. 6,149,919, 7,115,730 and 7,291,588).

Suitable adjuvants used to enhance an immune response further include, without limitation, MPL™ (3-O-deacylated monophosphoryl lipid A, Corixa, Hamilton, MT), which is described in U.S. Pat. No. 4,912,094. Also suitable for use as adjuvants are synthetic lipid A analogs or aminoalkyl glucosamine phosphate compounds (AGP), or derivatives or analogs thereof, which are available from Corixa (Hamilton, MT), and which are described in U.S. Pat. No. 6,113,918. One such AGP is 2-[(R)-3-Tetradecanoyloxytetradecanoylamino]ethyl 2-Deoxy-4-O-phosphono-3-O—[(R)-3-tetradecanoyoxytetradecanoyl]-2-[(R)-3-tetradecanoyloxytetradecanoyl-amino]-b-D-glucopyranoside, which is also known as 529 (formerly known as RC529). This 529 adjuvant is formulated as an aqueous form (AF) or as a stable emulsion (SE).

Suitable adjuvants also include, but are not limited to, surfactants, e.g., hexadecylamine, octadecylamine, lysolecithin, dimethyldioctadecylammonium bromide, N,N-dioctadecyl-N'—N-bis(2-hydroxyethyl-propane di-amine), methoxyhexadecyl-glycerol, and pluronic polyols; polanions, e.g., pyran, dextran sulfate, poly IC, polyacrylic acid, carbopol; peptides, e.g., muramyl dipeptide, MPL, aimethylglycine, tuftsin, oil emulsions, alum, and mixtures thereof. Other potential adjuvants include the B peptide subunits of *E. coli* heat labile toxin or of the cholera toxin. McGhee, J. R., et al., "On vaccine development," *Sem. Hematol.,* 30:3-15 (1993). Finally, the immunogenic product may be incorporated into liposomes for use in a vaccine formulation, or may be conjugated to proteins such as keyhole limpet hemocyanin (KLH) or human serum albumin (HSA) or other polymers.

In certain embodiments, the adjuvant comprises aluminum salt (e.g., aluminum hydroxide, aluminum phosphate, alum (potassium aluminum sulfate), or mixed aluminum salts). In certain embodiments, the adjuvant comprises a Toll like receptor agonist (e.g., monophosphoryl lipid A (MPL), a lipopeptide, and a synthetic nucleic acid sequence such as CpG and poly(I:C)). In certain embodiments, the adjuvant comprises squalene.

A polypeptide described herein can be conjugated or linked to another peptide or to a polysaccharide. For example, immunogenic proteins well-known in the art, also known as "carriers," may be employed. Useful immunogenic proteins include keyhole limpet hemocyanin (KLH), bovine serum albumin (BSA), ovalbumin, human serum albumin, human gamma globulin, chicken immunoglobulin G and bovine gamma globulin. Useful immunogenic polysaccharides include polysaccharides from other pathogens, such as those that are effective as vaccines. The immunogenic polysaccharides or proteins of other pathogens can be conjugated to, linked to, or mixed with the polypeptide described herein.

To prepare a vaccine, a polypeptide described herein can be isolated, lyophilized and stabilized. The polypeptide described herein may then be adjusted to an appropriate concentration, optionally combined with a suitable vaccine adjuvant, and packaged for use.

In certain embodiments, the present invention comprises two or more immunogenic polypeptides. In certain embodiments, one or more polypeptides are adjusted to an appropriate concentration and can be formulated with any suitable adjuvant, diluent, pharmaceutically acceptable carrier, or any combination thereof. As used herein the phrase "pharmaceutically acceptable carrier" is intended to include any and all solvents, dispersion media, coatings, antibacterial and antifungal agents, isotonic and absorption delaying agents, excipients and the like, compatible with pharmaceutical administration. The use of such media and agents for pharmaceutically active substances is well known in the art. Physiologically acceptable vehicles may be used as carriers and/or diluents. A pharmaceutically acceptable vehicle is understood to designate a compound or a combination of compounds entering into a pharmaceutical or immunogenic composition which does not cause side effects and which makes it possible, for example, to facilitate the administration of the active compound, to increase its life and/or its efficacy in the body, to increase its solubility in solution or alternatively to enhance its preservation. These pharmaceutically acceptable vehicles are well known and will be adapted by persons skilled in the art according to the nature and the mode of administration of the active compound chosen. These include, but are not limited to, water, Ringer's solution, an appropriate isotonic medium, glycerol, ethanol and other conventional solvents, phosphate buffered saline, and the like.

As used herein, the term "therapeutic agent" or "therapeutic complex" refers to any agent or material that has a beneficial effect on the mammalian recipient. Thus, "therapeutic agent" embraces both therapeutic and prophylactic molecules having nucleic acid or protein components.

"Antigen" refers to a molecule capable of being bound by an antibody. An antigen is additionally capable of being recognized by the immune system and/or being capable of inducing a humoral immune response and/or cellular immune response leading to the activation of B- and/or T-lymphocytes. An antigen can have one or more epitopes (B- and/or T-cell epitopes). Antigens as used herein may also be mixtures of several individual antigens. "Antigenic determinant" refers to that portion of an antigen that is specifically recognized by either B- or T-lymphocytes. B-lymphocytes responding to antigenic determinants produce antibodies, whereas T-lymphocytes respond to antigenic determinants by proliferation and establishment of effector functions critical for the mediation of cellular and/or humoral immunity.

The term, "antibody", is used herein in the broadest sense and specifically encompass monoclonal antibodies (including full length monoclonal antibodies), polyclonal antibodies, multispecific antibodies (e.g., bispecific antibodies), and antibody fragments such as variable domains and other portions of antibodies that exhibit a desired biological activity, e.g., SARS-CoV-2 binding and or neutralizing.

An "immune response" refers to a humoral immune response and/or cellular immune response leading to the activation or proliferation of B- and/or T-lymphocytes and/or and antigen presenting cells. In some instances, however, the immune responses may be of low intensity and become detectable only when using at least one substance in accordance with the invention. "Immunogenic" refers to an agent used to stimulate the immune system of a living organism, so that one or more functions of the immune system are increased and directed towards the immunogenic agent. An "immunogenic polypeptide" is a polypeptide that elicits a cellular and/or humoral immune response, whether alone or linked to a carrier. Preferably, antigen presenting cell may be activated.

A substance that "enhances" an immune response refers to a substance in which an immune response is observed that is greater or intensified or deviated in any way with the addition of the substance when compared to the same immune response measured without the addition of the substance. For example, the lytic activity of cytotoxic T cells can be measured, e.g. using a $^{51}Cr$ release assay, in samples obtained with and without the use of the substance during immunization. The amount of the substance at which the CTL lytic activity is enhanced as compared to the CTL lytic activity without the substance is said to be an amount sufficient to enhance the immune response of the animal to the antigen. In certain embodiments, the immune response in enhanced by a factor of at least about 2, such as by a factor of about 3 or more. The amount or type of cytokines secreted may also be altered. Alternatively, the amount of antibodies induced or their subclasses may be altered.

The terms "immunize" or "immunization" or related terms refer to conferring the ability to mount a substantial immune response (comprising antibodies and/or cellular immunity such as effector CTL) against a target antigen or epitope. These terms do not require that complete immunity be created, but rather that an immune response be produced which is substantially greater than baseline. For example, a mammal may be considered to be immunized against a target antigen if the cellular and/or humoral immune response to the target antigen occurs following the application of methods of the invention.

The term "immunotherapeutic" refers to a composition for the treatment of diseases, disorders or conditions. More specifically, the term is used to refer to a method of treatment wherein a beneficial immune response is generated by vaccination or by transfer of immune molecules. An "immunologically effective amount" refers to an amount of a composition sufficient to induce an immune response in an individual when introduced into that individual. In the context of active immunization, the term is synonymous with "immunogenically effective amount." The amount of a composition necessary to be immunologically effective varies according many factors including to the composition, the presence of other components in the composition, the antigen, the route of immunization, the individual, the prior immune or physiologic state etc.

The term "epitope" refers to basic element or smallest unit of recognition by an individual antibody or T-cell receptor, and thus the particular domain, region or molecular structure to which said antibody or T-cell receptor binds. An antigen may consist of numerous epitopes while a hapten, typically, may possess few epitopes. As used herein "correspond essentially to" refers to an epitope that will elicit an immunological response at least substantially equivalent to the response generated by the native epitope. An immunological response to a composition or vaccine is the development in the host of a cellular and/or antibody-mediated immune response to the polypeptide or vaccine of interest. Usually, such a response consists of the subject producing antibodies, B cell, helper T cells, suppressor T cells, and/or cytotoxic T cells directed specifically to an antigen or antigens included in the composition or vaccine of interest. Vaccines of the present invention can also include effective amounts of immunological adjuvants, known to enhance an immune response. An "effective amount" refers to an amount necessary or sufficient to realize a desired biologic effect. An effective amount of the composition would be the amount that achieves this selected result, and such an amount could be determined as a matter of routine by a person skilled in the art. For example, an effective amount for treating an immune system deficiency could be that amount necessary to cause activation of the immune system, resulting in the development of an antigen specific immune response upon exposure to antigen. The term is also synonymous with "sufficient amount." The effective amount for any particular application can vary depending on such factors as the disease or condition being treated, the particular composition being administered, the size of the subject, and/or the severity of the disease or condition. One of ordinary skill in the art can empirically determine the effective amount of a particular composition of the present invention without necessitating undue experimentation.

Methods of Producing a Cell or Recombinant Polypeptide of the Invention

Certain embodiments of the invention provide a method of making a genetically modified cell capable of producing a polypeptide described herein, the method comprising transfecting or transducing a cell with a nucleic acid, expression cassette or vector described herein. In certain embodiments, the vector comprises a selectable marker. In certain embodiments, the vector is a lentivirus vector.

Certain embodiments also provide a method of producing a polypeptide described herein (e.g., a recombinant polypeptide comprising a SARS-CoV-2 RBD), comprising transfecting or transducing a cell with a nucleic acid, expression cassette or vector described herein. In certain embodiments, the vector comprises a selectable marker. In certain embodiments, the vector is a lentivirus vector.

In certain embodiments, the cell is a mammalian cell. In certain embodiments, the cell is a 293F cell. In certain embodiments, the cell is a cell described herein.

In certain embodiments, the method further comprises culturing the cell under appropriate conditions and for a sufficient time to allow expression of the recombinant polypeptide to occur. In certain embodiments, the cell is cultured for about 12 h, 18 h, 24 h, 36 h, 48 h, 3 days, 4 days, 5 days, 6 days, 1 week, 2 weeks, 3 weeks, 4 weeks or more.

In some embodiments, a selectable marker is used to select cells that have been successfully transfected/transduced. As a non-limiting example, antibiotic resistance (e.g., to puromycin or another antibiotic) can be used to select genetically modified cells that contain an expression construct of interest.

In certain embodiments, the cell is stably transfected. In certain embodiments, the cell is stably transduced.

In certain embodiments, the method further comprises isolating the recombinant polypeptide from the cell, cellular components and/or the growth media.

In certain embodiments, the cell secretes the recombinant polypeptide into the cell growth media. In certain embodiments, the recombinant polypeptide is isolated from the growth media.

In certain embodiments, the method further comprises purifying the isolated recombinant polypeptide. In certain embodiments, the recombinant polypeptide is purified using an affinity column (e.g., a Nickel affinity column). In certain embodiments, the recombinant polypeptide is purified using gel filtration. In certain embodiments, the recombinant polypeptide is purified using an ion exchange column.

In certain embodiments, isolated recombinant polypeptide is substantially pure. For example, in certain embodiments, the isolated recombinant polypeptide comprises less than about 30% contaminants, such as host cell proteins or growth media. In certain embodiments, the isolated recombinant polypeptide comprises less than about 25%, 20%, 15%, 14%, 13%, 12%, 11%, 10%, 9%, 8%, 7%, 6%, 5%, 4%, 3%, 2%, 1%, 0.9%, 0.8%, 0.7%, 0.6%, 0.5%, 0.4%, 0.5%, 0.4%, 0.3%, 0.2%, 0.1% or less of contaminants, such as host cell proteins or growth media.

In certain embodiments, a method described herein may be used to produce a polypeptide as described herein 1) that is biologically active (e.g., capable of binding to ACE2 with, e.g., high affinity and specificity) and/or 2) which is properly folded. Thus, in certain embodiments, the produced polypeptide is capable of binding to ACE2. In certain embodiments, the produced polypeptide is properly folded.

In certain embodiments, a method described herein may be used to produce a high yield of a polypeptide of the invention. For example, in certain embodiments, the method produces at least about 30 mg/liter cell culture of the polypeptide. In certain embodiments, the method produces at least about 35 mg/liter cell culture of the polypeptide. In certain embodiments, the method produces at least about 40 mg/liter cell culture of the polypeptide. In certain embodiments, the method produces at least about 45 mg/liter cell culture of the polypeptide. In certain embodiments, the method produces at least about 50 mg/liter cell culture of the polypeptide. In certain embodiments, the method produces at least about 55 mg/liter cell culture of the polypeptide. In certain embodiments, the method produces at least about 60 mg/liter cell culture of the polypeptide. In certain embodiments, the method produces at least about 65 mg/liter cell culture of the polypeptide. In certain embodiments, the method produces at least about 70 mg/liter cell culture of the polypeptide. In certain embodiments, the method produces about 30 mg/liter cell culture to about 70 mg/liter cell culture of the polypeptide. In certain embodiments, the method produces about 35 mg/liter cell culture to about 65 mg/liter cell culture of the polypeptide. In certain embodiments, the method produces about 40 mg/liter cell culture to about 60 mg/liter cell culture of the polypeptide.

Methods of Use

As described herein, a polypeptide described herein may be used for diagnostic and therapeutic purposes (e.g., vaccination), as well as for antibody production and screening assays.

Methods of Treatment Certain embodiments of the invention provide a polypeptide that is capable of competitively binding to ACE-2, which limits viral access to the receptor and leads to the inhibition of SARS-Cov-2 virus cellular binding and entry. Accordingly, certain embodiments of the invention provide a method for preventing a SARS-Cov-2 virus particle from binding to ACE2, the method comprising contacting an ACE2 expressing cell with a polypeptide described herein under conditions suitable for binding between the polypeptide and ACE2, thereby preventing binding between ACE2 and a SARS-CoV-2 virus particle. In certain embodiments, the cell is contacted in vitro, in vivo or ex vivo. In certain embodiments, the cell is contacted in vitro. In certain embodiments, the cell is contacted in vivo (e.g., by administration to an animal). In certain embodiments, the cell and polypeptide are contacted in the presence of a SARS-CoV-2 virus particle.

Certain embodiments also provide a method of protecting a susceptible animal (e.g., a mammal, such as a human) against a SARS-CoV-2 infection comprising administering to the animal an effective amount of a polypeptide or composition described herein.

Certain embodiments also provide a method of immunizing an animal (e.g., a mammal, such as a human) against a SARS-CoV-2 infection comprising administering to the animal an effective amount of a polypeptide or composition described herein.

Certain embodiments also provide a method of treating or preventing a SARS-CoV-2 infection in an animal (e.g., a mammal, such as a human) comprising administering to the animal an effective amount of a polypeptide or composition described herein.

In certain embodiments, the polypeptide or composition is administered by intramuscular, intradermal, subcutaneous, pulmonary delivery, or via a mucosal surface. In certain embodiments, the polypeptide or composition is administered by oral ingestion. In certain embodiments, the polypeptide or composition is administered intranasally.

Certain embodiments of the invention also provide the use of a polypeptide or composition described herein for use in medical therapy.

Certain embodiments of the invention provide a polypeptide or composition described herein for use in 1) protecting a susceptible animal against a SARS-CoV2 infection; 2) immunizing an animal against a SARS-CoV2 infection; and/or 3) treating or preventing a SARS-CoV-2 infection in an animal.

Certain embodiments of the invention also provide the use of polypeptide or composition described herein to prepare a medicament for 1) protecting a susceptible animal against a SARS-CoV2 infection; 2) immunizing an animal against a SARS-CoV2 infection; and/or 3) treating or preventing a SARS-CoV-2 infection in an animal.

Certain embodiments of the invention provide a method of treating or preventing a SARS-CoV-2 infection in an animal (e.g., a mammal, such as a human) comprising 1) administering to the animal serum collected from a non-human animal that had been administered a polypeptide or composition described herein.

Certain embodiments of the invention also provide a method of treating or preventing a SARS-CoV-2 infection in a subject (e.g., a mammal, such as a human) comprising 1) administering a polypeptide or composition described herein to a non-human animal; 2) collecting serum from the non-human animal; and 3) administering the serum to the subject.

Certain embodiments of the invention provide serum collected from a non-human animal that had been administered a polypeptide or composition described herein for use in treating or preventing a SARS-CoV-2 infection in a subject, such as a human.

Certain embodiments of the invention also provide the use of serum collected from a non-human animal that had been administered a polypeptide or composition described herein to prepare a medicament for treating or preventing a SARS-CoV-2 infection in a subject, such as a human.

Diagnostic Methods

Certain embodiments of the invention provide a method of detecting an anti-SARS-CoV-2 antibody in a test sample, the method comprising contacting the test sample with a polypeptide or composition as described herein. In certain embodiments, the sample and the polypeptide or composition are contacted under conditions suitable for an anti-SARS-CoV-2 antibody to bind to the polypeptide. In certain embodiments, the method further comprises detecting a bound anti-SARS-CoV-2 antibody. In certain embodiments, the method comprises measuring anti-SARS-CoV-2 antibody titers in the sample. In certain embodiments, the sample is from a subject that has or had COVID-19. In certain embodiments, the sample is from a subject that was vaccinated against SARS-CoV-2.

Certain embodiments of the invention also provide a method of identifying a subject that has or has had a SARS-CoV2 infection, the method comprising contacting a test sample from the subject with a polypeptide or composition described herein and detecting the presence or absence of an anti-SARS-CoV2 antibody in the test sample, wherein the subject is identified as having or having had a SARS-CoV2 infection when the presence of an anti-SARS-CoV2 antibody is detected.

Certain embodiments of the invention provide a method of diagnosing a subject as having or having had a SARS-CoV2 infection, the method comprising 1) obtaining a biological sample from the subject; 2) contacting the sample with a polypeptide or composition described herein and detecting whether anti-SARS-CoV-2 antibodies are present in the sample; and 3) diagnosing the subject as having or having had a SARS-CoV2 infection when anti-SARS-CoV-2 antibodies are detected.

In certain embodiments, a method described herein further comprises administering a therapeutic agent (e.g., antiviral agent, such as Remdesivir, or an antibody therapy) to the subject (e.g., the diagnosed subject).

A polypeptide described herein is readily applicable in antigen-antibody reactions with an antibody that is capable of binding to SARS-Cov-2 RBD. Thus, in certain embodiments, anti-SARS-CoV-2 antibodies are detected using an immunoassay, such as an immunoassay described herein. Typical immunoassay methods of antigen-antibody reactions include, but are not limited to, immunodiffusion assay, immunoelectrophoresis, agglutination assay, enzyme immunoassays and radioimmunoassay (RIA).

In certain embodiments, the immunoassay method is an ELISA based method. In certain embodiments, the ELISA is an antigen-down ELISA. In certain embodiments, the ELISA is a capture assay also referred to as sandwich ELISA. In certain embodiments, the immunoassay method is a chemiluminescence based method.

In certain embodiments, the immunoassay method is conducted manually. In certain embodiments, the immunoassay method is conducted within an automated immunoassay system (e.g., a high throughput immunoassay automation system).

In certain embodiments, a test sample is contacted with the polypeptide or composition described herein for a first period. In certain embodiments, the polypeptide is immobilized on a solid substrate for a first period. In certain embodiments, the polypeptide described herein is directly immobilized on a solid substrate (e.g., adsorbed or chemically conjugated on a solid substrate). In certain embodiments, a polypeptide described herein is indirectly immobilized on a solid substrate via a capture agent (e.g., a capture antibody from the solid substrate in a sandwich ELISA). In certain embodiments, the polypeptide described herein is indirectly immobilized on a solid substrate via an anti-tag antibody. In certain embodiments, the polypeptide described herein is indirectly immobilized on an anti-tag antibody (e.g., anti-His tag antibody) pre-coated ELISA plate. In certain embodiments, the polypeptide described herein is indirectly immobilized on an anti-tag antibody (e.g., anti-His tag antibody) conjugated particle (e.g., magnetic particle), for example, in a chemiluminescence immunoassay.

In certain embodiments, the method comprises one or more washing steps after the first period.

In certain embodiments, the method comprises contacting the solid substrate with an enzyme-linked detection agent (e.g., alkaline phosphatase (ALP) or horseradish peroxidase (HRP) linked anti-IgG, anti-IgM or anti-IgA antibody) for a second period.

In certain embodiments, the method comprises one or more washing steps after the second period.

In certain embodiments, the method comprises contacting the solid substrate with a signal development agent (e.g., luminol, TMB, OPD) for a third period to produce detectable signal (e.g., luminescent light signal or chromogenic signal).

In certain embodiments, the test sample is a biological sample. In certain embodiment, the test sample is blood, plasma, serum, saliva, tears, feces and lavage (e.g., bronchoalveolar lavage). In certain embodiment, the test sample is serum.

In certain embodiments, the test sample is a clinically acquired biological sample. In certain embodiments, the test sample is a non-clinical research and development sample.

In certain embodiments, the anti-SARS-CoV-2 antibody is an IgM antibody. In certain embodiments, the anti-SARS-CoV-2 antibody is an IgA antibody. In certain embodiments, the anti-SARS-CoV-2 antibody is an IgG antibody. In certain embodiments, the anti-SARS-CoV-2 antibody is an IgG1 antibody. In certain embodiments, the anti-SARS-CoV-2 antibody is an IgG2 antibody. In certain embodiments, the anti-SARS-CoV-2 antibody is an IgG3 antibody. In certain embodiments, the anti-SARS-CoV-2 antibody is an IgG4 antibody.

Antibody Production and Screening Methods

As described herein, certain embodiments of the invention provide a method of generating and/or screening for a protective SARS-Cov-2 neutralizing agent using a polypeptide of the invention. In certain embodiments, the agent is antibody or a fragment thereof. In certain embodiments, the agent is an aptamer. In certain embodiments, the agent is an affibody or nanobody. In certain embodiments, the agent is anti-serum.

Accordingly, certain embodiments provide a method for producing an anti-SARS-CoV-2 antibody in a subject (e.g., a non-human animal), the method comprising administering to the subject a polypeptide described herein; and isolating the antibody or B cell(s) from the animal. Certain embodiments also provide a method for producing an anti-SARS-CoV-2 antibody, the method comprising screening a phage antibody/nanobody library against the polypeptide described herein (e.g., immobilized on a solid surface) and isolating the binder(s). Other embodiments provide an anti-SARS-CoV2 antibody produced using a method as described herein.

In certain embodiments, the subject is a non-human animal, such as a rodent. In certain embodiments, the subject is a mouse. In certain embodiments, the subject is a humanized mouse capable of producing human antibody. In certain embodiments, the subject is a rat. In certain embodiments, the subject is a rabbit. In certain embodiments, the subject is a hamster. In certain embodiments, the subject is a chicken. In certain embodiments, the subject is a goat. In certain embodiments, the subject is a horse.

For immunization with the polypeptide, a number of different protocols known in the art may be used. In certain embodiments, the subject is administered the polypeptide more than one time (e.g., over a period of days, weeks or months). For administration of the polypeptide, any suitable route may be used, such as injection (e.g., intramuscular, intraperitoneal injection). In certain embodiments, the polypeptide is administered with an adjuvant. In certain embodiments, the polypeptide is present in a composition described herein.

Following immunization, antigen-specific B cells may be harvested. Monoclonal antibodies may be generated using methods known in the art.

A polypeptide described herein may also be used to screen/characterize potential anti-SARS-CoV2 antibodies (e.g., for affinity or specificity). Accordingly, certain embodiments also provide a method for screening an antibody for affinity and/or specificity to SARS-CoV2, the method comprising contacting the antibody with a polypeptide described herein and measuring binding between the antibody and the polypeptide.

In certain embodiments, the binding strength or affinity is measured via an ELISA based assay or a SPR based assay.

Certain embodiments of the invention provide a method of screening for a SARS-Cov-2 neutralizing agent comprising contacting a polypeptide described herein with a display library (e.g., phage surface display, yeast surface display, ribosomal display) and selecting a binder(s) that has affinity or specificity for the polypeptide.

Certain embodiments of the invention provide a method of screening for a SARS-Cov-2 neutralizing antibody comprising contacting a polypeptide described herein with B cell(s) and selecting the B cell that has affinity or specificity for the polypeptide.

In certain embodiments, a polypeptide described herein is labeled with a detectable agent, such as a fluorochrome, for sorting or for selecting a B cell that express a neutralizing antibody against SARS-Cov-2 RBD (e.g., via flow cytometry).

In certain embodiments, a polypeptide described herein is immobilized onto a magnetic particle for magnetically sorting or for selecting a B cell that expresses a neutralizing antibody against SARS-Cov-2 RBD.

In certain embodiments, anti-SARS-Cov-2 antibodies can be enriched or purified from the anti-serum or plasma of an animal (e.g., immunized non-human animal, or a clinically SARS-Cov-2 convalescent human) via contacting the polypeptide described herein that is immobilized on an affinity column.

Kits

Certain embodiments of the invention provide a kit comprising:

1) a polypeptide as described herein or a composition as described herein;
2) packaging material; and
3) instructions for using or administering the polypeptide or composition, e.g., as described in a method herein. In certain embodiments, the kit further comprises one or more additional therapeutic agents.

Certain embodiments of the invention provide a kit comprising:

1) a polypeptide described herein in a lyophilized formulation or a liquid formulation;
2) packaging material; and
3) instructions to reconstitute the polypeptide and/or to conjugate the polypeptide onto a substrate or other agent.

In certain embodiments, the kit further comprises optional components selected from the group consisting of an ELISA plate, a coating buffer, a blocking buffer, a diluent, a washing solution, a detection agent and a signal development agent as described above, a magnetic particle, a chromatography column, and an activating agent for conjugation to a fluorochrome.

Certain embodiments of the invention provide a kit comprising:

1) an ELISA plate coated with the polypeptide described herein;
2) packaging material; and
3) instructions to conduct an ELISA immunoassay.

In certain embodiments, the kit further comprises optional reagents selected from the group consisting of a blocking buffer, a diluent, a washing solution, a detection agent and signal development agent as described above.

Certain embodiments of the invention provide a kit comprising:

1) an ELISA plate coated with an anti-tag capture antibody (e.g., anti-His tag antibody);
2) a polypeptide as described herein or a composition as described herein;
3) packaging material; and
4) instructions to conduct an ELISA immunoassay.

Certain embodiments of the invention provide a kit comprising:

1) magnetic particles conjugated with a polypeptide described herein;
2) packaging material; and
3) instructions to conduct the immunoassay.

Administration

In certain embodiments, an effective amount of a polypeptide or composition described herein is administered to the subject. "Effective amount" or "therapeutically effective amount" are used interchangeably herein, and refer to an amount of a compound, formulation, material, or composition, as described herein effective to achieve a particular biological result. Such results may include, but are not limited to the inhibition of virus infection as determined by any means suitable in the art.

In certain embodiments, an amount of the vaccine is administered in order to immunize to the subject. As used herein, "immunization" or "vaccination" are used interchangeably herein and are intended for prophylactic or therapeutic immunization or vaccination.

In certain embodiments, a polypeptide or composition described herein is administered via intramuscular, intradermal, or subcutaneous delivery. In certain embodiments, a polypeptide or composition described herein is administered via a mucosal surface, such as an oral, or intranasal surface. In certain embodiments, a polypeptide or composition described herein is administered via intrasternal injection, or by using infusion techniques.

In certain embodiments, "pharmaceutically acceptable" refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability. "Pharmaceutically acceptable carrier" refers to a medium that does not interfere with the effectiveness of the biological activity of the active ingredient(s) and is not toxic to the host to which it is administered.

The polypeptides and compositions of the invention may be formulated as pharmaceutical compositions and administered to a mammalian host, such as a human patient, in a variety of forms adapted to the chosen route of administration, i.e., orally, intranasally, intradermally or parenterally, by intravenous, intramuscular, topical or subcutaneous routes.

Thus, the present polypeptides may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the polypeptides may be combined with one or more excipients and used in the form of ingestible tablets, buccal tablets, troches, capsules, elixirs, suspensions, syrups, wafers, and the like. Such compositions and preparations should contain at least 0.1% of polypeptides. The percentage of the compositions and preparations may, of course, be varied and may conveniently be between about 2 to about 60% of the weight of a given unit dosage form. The amount of the polypeptides in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the polypeptides, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the polypeptides may be incorporated into sustained-release preparations and devices.

The polypeptides may also be administered intravenously or intraperitoneally by infusion or injection. Solutions of the polypeptides can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the polypeptides which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the polypeptides in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the polypeptides plus any additional desired ingredient present in the previously sterile-filtered solutions.

For topical administration, the present polypeptides may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present polypeptides can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. Examples of useful dermatological compositions which can be used to deliver the polypeptides to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

To immunize a subject, a polypeptide described herein is administered parenterally, usually by intramuscular or subcutaneous injection in an appropriate vehicle. Other modes of administration, however, such as oral delivery or intranasal delivery, are also acceptable. Vaccine formulations will contain an effective amount of the active ingredient in a vehicle.

Formulations will contain an effective amount of the active ingredient in a vehicle, the effective amount being readily determined by one skilled in the art. The active ingredient may typically range from about 1% to about 95% (w/w) of the composition, or even higher or lower if appropriate. The amount for any particular application can vary depending on such factors as the severity of the condition. The quantity to be administered depends upon factors such as the age, weight and physical condition of the animal considered for vaccination and kind of concurrent treatment, if any. The quantity also depends upon the capacity of the animal's immune system to synthesize antibodies, and the degree of protection desired. Typically, dosages used in vitro may provide useful guidance in the amounts useful for in situ administration of the composition, and animal models may be used to determine effective dosages for treatment of particular disorders. Various considerations are described, e.g., in Gilman et al., eds., Goodman And Gilman's: The Pharmacological Bases of Therapeutics, 8th ed., Pergamon Press, 1990; and Reminpton's Pharmaceutical Sciences, 17th ed., Mack Publishing Co., Easton, Pa., 1990, each of which is herein incorporated by reference. Additionally, effective dosages can be readily established by one of ordinary skill in the art through routine trials establishing dose response curves. The subject is immunized by administration of the composition thereof in one or more doses. Multiple doses may be administered as is required to maintain a state of immunity to the target. For example, the initial dose may be followed up with a booster dosage after a period of about four weeks to enhance the immunogenic response. Further booster dosages may also be administered. The composition may be administered multiple (e.g., 2, 3, 4 or 5) times at an interval of, e.g., about 1, 2, 3, 4, 5, 6 or 7, 14, or 21 days apart.

Intranasal formulations may include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

Oral liquid preparations may be in the form of, for example, aqueous or oily suspension, solutions, emulsions, syrups or elixirs, or may be presented dry in tablet form or a product for reconstitution with water or other suitable vehicle before use. Such liquid preparations may contain conventional additives such as suspending agents, emulsifying agents, non-aqueous vehicles (which may include edible oils), or preservative.

Thus, the present compositions may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the present compositions may be combined with one or more excipients and used in the form of ingestible tablets, buccal tablets, troches, capsules, elixirs, suspensions, syrups, wafers, and the like. Such preparations should contain at least 0.1% of the present composition. The percentage of the compositions may, of course, be varied and may conveniently be between about 2 to about 60% of the weight of a given unit dosage form. The amount of present composition in such therapeutically useful preparations is such that an effective dosage level will be obtained.

Useful dosages of the compositions of the present invention can be determined by comparing their in vitro activity, and in vivo activity in animal models. The amount of the compositions described herein required for use in treatment will vary with the route of administration and the age and condition of the subject and will be ultimately at the discretion of the attendant veterinarian or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Polypeptides of the invention can also be administered in combination with other therapeutic agents. Accordingly, one embodiment the invention also provides a composition comprising a polypeptide, at least one other therapeutic agent, and a pharmaceutically acceptable diluent or carrier.

CERTAIN EMBODIMENTS

Embodiment 1. An isolated or purified polypeptide comprising a SARS-CoV-2 receptor binding domain (RBD) operably linked to a peptide tag (e.g., an affinity tag).

Embodiment 2. The polypeptide of embodiment 1, wherein the SARS-CoV-2 RBD comprises an amino acid sequence having at least about 90% sequence identity to SEQ ID NO:2.

Embodiment 3. The polypeptide of embodiment 1, wherein the SARS-CoV-2 RBD comprises an amino acid sequence having at least about 95% sequence identity to SEQ ID NO:2.

Embodiment 4. The polypeptide of embodiment 1, wherein the SARS-CoV-2 RBD comprises an amino acid sequence having at least about 99% sequence identity to SEQ ID NO:2.

Embodiment 5. The polypeptide of embodiment 1, wherein the SARS-CoV-2 RBD comprises SEQ ID NO:2.

Embodiment 6. The polypeptide of any one of embodiments 1-5, wherein the SARS-CoV-2 RBD is between about 207 to about 227 amino acids in length.

Embodiment 7. The polypeptide of any one of embodiments 1-5, wherein the SARS-CoV-2 RBD is between about 213 to about 221 amino acids in length.

Embodiment 8. The polypeptide of any one of embodiments 1-5, wherein the SARS-CoV-2 RBD is between about 215 to about 219 amino acids in length.

Embodiment 9. The polypeptide of any one of embodiments 1-5, wherein the SARS-CoV-2 RBD is 217 amino acids in length.

Embodiment 10. The polypeptide of embodiment 9, wherein the SARS-CoV-2 RBD consists of SEQ ID NO:2.

Embodiment 11. An isolated or purified polypeptide comprising a SARS-CoV-2 receptor binding domain (RBD) linked directly or through a linker group to a peptide tag (e.g., an affinity tag), wherein the SARS-CoV-2 RBD is between about 197 to about 237 amino acids in length.

Embodiment 12. The polypeptide of embodiment 11, wherein the SARS-CoV-2 RBD comprises an amino acid sequence having at least about 90% sequence identity to SEQ ID NO:5.

Embodiment 13. The polypeptide of embodiment 11, wherein the SARS-CoV-2 RBD comprises an amino acid sequence having at least about 90% sequence identity to SEQ ID NO:2

Embodiment 14. The polypeptide of embodiment 13, wherein the SARS-CoV-2 RBD comprises an amino acid sequence having at least about 95% sequence identity to SEQ ID NO:2.

Embodiment 15. The polypeptide of embodiment 13, wherein the SARS-CoV-2 RBD comprises an amino acid sequence having at least about 99% sequence identity to SEQ ID NO:2.

Embodiment 16. The polypeptide of embodiment 13, wherein the SARS-CoV-2 RBD comprises or consists of SEQ ID NO:2.

Embodiment 17. An isolated or purified polypeptide comprising a SARS-CoV-2 receptor binding domain (RBD) linked directly or through a linker group to a peptide tag (e.g., an affinity tag), wherein the SARS-CoV-2 RBD is between about 197 to about 237 amino acids in length; and wherein the SARS-CoV-2 RBD comprises at least 90% identity to a sequence corresponding to SEQ ID NO:5, or wherein the SARS-CoV-2 RBD comprises at least 90% identity to the sequence corresponding to SEQ ID NO:2.

Embodiment 18. The polypeptide of embodiment 17, wherein the SARS-CoV-2 RBD comprises at least 90% identity to the sequence corresponding to SEQ ID NO:5, and wherein from 1 to 10 amino acids located at positions 1-10 in reference to the sequence corresponding to SEQ ID NO:5 are not comprised within the SARS-CoV-2 RBD amino acid sequence.

Embodiment 19. The polypeptide of embodiment 17, wherein the SARS-CoV-2 RBD comprises at least 90% identity to a sequence corresponding to SEQ ID NO:5, and wherein from 1 to 10 amino acids located at positions 228-237 in reference to the sequence corresponding to SEQ ID NO:5 are not comprised within the SARS-CoV-2 RBD amino acid sequence.

Embodiment 20. The polypeptide of embodiment 17, wherein the SARS-CoV-2 RBD comprises at least 90% identity to the sequence corresponding to SEQ ID NO:5, and wherein from 1 to 10 amino acids located at positions 1-10 in reference to the sequence corresponding to SEQ ID NO:5 are not comprised within the SARS-CoV-2 RBD amino acid sequence, and wherein from 1 to 10 amino acids located at positions 228-237 in reference to the sequence corresponding to SEQ ID NO:5 are not comprised within the SARS-CoV-2 RBD amino acid sequence.

Embodiment 21. The polypeptide of embodiment 17, wherein the SARS-CoV-2 RBD comprises at least 90% identity to the sequence corresponding to SEQ ID NO:2, and wherein from 1 to 10 amino acids located at positions 1-10 in reference to the sequence corresponding to SEQ ID NO:2 are not comprised within the SARS-CoV-2 RBD amino acid sequence.

Embodiment 22. The polypeptide of embodiment 17, wherein the SARS-CoV-2 RBD comprises at least 90% identity to the sequence corresponding to SEQ ID NO:2, and wherein from 1 to 10 amino acids located at positions 208-217 in reference to the sequence corresponding to SEQ ID NO:2 are not comprised within the SARS-CoV-2 RBD amino acid sequence.

Embodiment 23. The polypeptide of embodiment 17, wherein the SARS-CoV-2 RBD comprises at least 90% identity to the sequence of SEQ ID NO:2, and wherein from 1 to 10 amino acids located at positions 1-10 in reference to the sequence corresponding to SEQ ID NO:2 are not comprised within the SARS-CoV-2 RBD amino acid sequence, and wherein from 1 to 10 amino acids located at positions 208-217 in reference to the sequence corresponding to SEQ ID NO:2 are not comprised within the SARS-CoV-2 RBD amino acid sequence.

Embodiment 24. An isolated or purified polypeptide comprising a SARS-CoV-2 receptor binding domain (RBD) linked directly or through a linker group to a peptide tag (e.g., an affinity tag), wherein the SARS-CoV-2 RBD is between about 197 to about 237 amino acids in length; and wherein the SARS-CoV-2 RBD comprises at least 90% identity to a sequence corresponding to SEQ ID NO:10.

Embodiment 25. The polypeptide of embodiment 24, wherein the SARS-CoV-2 RBD further comprises from 1 to 10 amino acids provided in a sequence corresponding to SEQ ID NO:11.

Embodiment 26. The polypeptide of embodiment 24, wherein the SARS-CoV-2 RBD further comprises from 1 to 10 amino acids provided in a sequence corresponding to SEQ ID NO:12.

Embodiment 27. The polypeptide of embodiment 24, wherein the SARS-CoV-2 RBD further comprises 1 to 10 amino acids provided in a sequence corresponding to SEQ ID NO:11, and further comprises from 1 to 10 amino acids provided in a sequence corresponding to SEQ ID NO:12.

Embodiment 28. An isolated or purified polypeptide comprising a SARS-CoV-2 receptor binding domain (RBD) linked directly or through a linker group to a peptide tag (e.g., an affinity tag), wherein the SARS-CoV-2 RBD is between about 197 to about 237 amino acids in length; and wherein the SARS-CoV-2 RBD comprises at least 90% identity to a sequence corresponding to SEQ ID NO:2.

Embodiment 29. The polypeptide of embodiment 28, wherein the SARS-CoV-2 RBD further comprises from 1 to 10 amino acids provided in the sequence corresponding to SEQ ID NO:13.

Embodiment 30. The polypeptide of embodiment 28, wherein the SARS-CoV-2 RBD further comprises from 1 to 10 amino acids provided in the sequence corresponding to SEQ ID NO:14.

Embodiment 31. The polypeptide of embodiment 28, wherein the SARS-CoV-2 RBD further comprises 1 to 10 amino acids provided in the sequence corresponding to SEQ ID NO:13, and further comprises from 1 to 10 amino acids provided in the sequence corresponding to SEQ ID NO:14.

Embodiment 32. The polypeptide of any one of embodiments 11-31, wherein the SARS-CoV-2 RBD comprises an amino acid sequence having at least about 95% sequence identity to SEQ ID NO:2 or SEQ ID NO:5.

Embodiment 33. The polypeptide of any one of embodiments 11-31, wherein the SARS-CoV-2 RBD comprises an amino acid sequence having at least about 99% sequence identity to SEQ ID NO:2 or SEQ ID NO:5.

Embodiment 34. The polypeptide of embodiment 33, wherein the SARS-CoV-2 RBD comprises or consists of SEQ ID NO:2.

Embodiment 35. The polypeptide of any one of embodiments 1-34, wherein the SARS-CoV-2 RBD is between about 207 to about 227 amino acids in length.

Embodiment 36. The polypeptide of any one of embodiments 1-34, wherein the SARS-CoV-2 RBD is between about 213 to about 221 amino acids in length.

Embodiment 37. The polypeptide of any one of embodiments 1-34, wherein the SARS-CoV-2 RBD is between about 215 to about 219 amino acids in length.

Embodiments 38. The polypeptide of any one of embodiments 1-34, wherein the SARS-CoV-2 RBD is 217 amino acids in length.

Embodiment 43. The polypeptide of embodiment 42, wherein the poly(His) tag is a 8×His tag (SEQ ID NO: 6).

Embodiment 40. The polypeptide of any one of embodiments 1-39, wherein the peptide tag is an affinity tag.

Embodiment 41. The polypeptide of embodiment 40, wherein the affinity tag is a poly(His) tag, FLAG, 3× FLAG, c-Myc, Fc tag, or a hemagglutinin tag (e.g. HA).

Embodiment 42. The polypeptide of embodiment 41, wherein the affinity tag is a poly(His) tag.

Embodiment 43. The polypeptide of embodiment 42, wherein the poly(His) tag is a 8× His tag.

Embodiment 44. The polypeptide of any one of embodiments 1-43, wherein the SARS-CoV-2 RBD amino acid sequence is linked directly to the peptide tag (e.g., affinity tag; e.g., through a peptide bond).

Embodiment 45. The polypeptide of any one of embodiments 1-43, wherein the SARS-CoV-2 RBD amino acid sequence is linked to the peptide tag (e.g., affinity tag) through a linker group (e.g., an amino acid linker group).

Embodiment 46. The polypeptide of any one of embodiments 1-45, wherein the peptide tag (e.g., affinity tag) is linked to the N-terminus of the SARS-CoV-2 RBD amino acid sequence.

Embodiment 47. The polypeptide of any one of embodiments 1-45, wherein the peptide tag (e.g., affinity tag) is linked to the C-terminus of the SARS-CoV-2 RBD amino acid sequence.

Embodiment 48. The polypeptide of any one of embodiments 1-47, wherein the polypeptide further comprises a signal peptide sequence, wherein the signal peptide sequence is operably linked to the SARS-CoV-2 RBD amino acid sequence.

Embodiment 49. The polypeptide of any one of embodiments 1-48, wherein the polypeptide comprises an amino acid sequence having at least about 90% identity to SEQ ID NO:3 or SEQ ID NO:4.

Embodiment 50. The polypeptide of any one of embodiments 1-48, wherein the polypeptide comprises an amino acid sequence having at least about 95% identity to SEQ ID NO:3 or SEQ ID NO:4.

Embodiment 51. The polypeptide of any one of embodiments 1-48, wherein the polypeptide comprises an amino acid sequence having at least about 99% identity to SEQ ID NO:3 or SEQ ID NO:4.

Embodiment 52. The polypeptide of any one of embodiments 1-48, wherein the polypeptide comprises SEQ ID NO:3 or SEQ ID NO:4.

Embodiment 53. The polypeptide of any one of embodiments 1-48, wherein the polypeptide comprises SEQ ID NO:3.

Embodiment 54. The polypeptide of embodiment 53, which consists of SEQ ID NO:3.

Embodiment 55. The polypeptide of any one of embodiments 1-48, wherein the polypeptide comprises SEQ ID NO:4.

Embodiment 56. The polypeptide of embodiment 55, which consists of SEQ ID NO:4.

Embodiment 57. The polypeptide of any one of embodiments 1-56, which is capable of binding to angiotensin-converting enzyme 2 (ACE2).

Embodiment 58. The polypeptide of any one of embodiments 1-57, which is operably linked to a solid substrate.

Embodiment 59. The polypeptide of embodiment 58, which is immobilized on a solid substrate.

Embodiment 60. A composition comprising a polypeptide as described in any one of embodiments 1-59 and a carrier.

Embodiment 61. The composition of embodiment 60, which is a pharmaceutical composition comprising a pharmaceutically acceptable carrier.

Embodiment 62. An isolated polynucleotide comprising a nucleotide sequence encoding the polypeptide of any one of embodiments 1-57.

Embodiment 63. The polynucleotide of embodiment 62, which comprises a nucleic acid sequence having at least about 90% sequence identity to SEQ ID NO: 1.

Embodiment 64. An expression cassette comprising a promoter operably linked to the polynucleotide of embodiment 62 or 63.

Embodiment 65. A vector comprising the polynucleotide of embodiment 62 or 63 or the expression cassette of embodiment 64.

Embodiment 66. A cell comprising the polynucleotide of embodiment 62 or 63, the expression cassette of embodiment 64 or the vector of embodiment 65.

Embodiment 67. The cell of embodiment 66, which is a mammalian cell.

Embodiment 68. The cell of embodiment 67, which is a human embryonic kidney (HEK) 293 cell (e.g., a 293F cell).

Embodiment 69. A method of making a cell as described in any one of embodiments 66-68, the method comprising transfecting or transducing the cell with the polynucleotide of embodiment 62 or 63, the expression cassette of embodiment 64 or the vector of embodiment 65.

Embodiment 70. The method of embodiment 69, further comprising using a selectable marker to select a cell that comprises the polynucleotide of embodiment 62 or 63, the expression cassette of embodiment 64 or the vector of embodiment 65.

Embodiment 71. A method of producing a polypeptide, the method comprising transfecting or transducing a cell with the polynucleotide of embodiment 62 or 63, the expression cassette of embodiment 64 or the vector of embodiment 65.

Embodiment 72. The method of embodiment 71, wherein the cell is a mammalian cell.

Embodiment 73. The method of embodiment 72, wherein the cell is a human embryonic kidney (HEK) 293 cell (e.g., a 293F cell).

Embodiment 74. The method of any one of embodiments 71-73, further comprising culturing the cell under appropriate conditions for expression of the polypeptide.

Embodiment 75. A method of producing a polypeptide, the method comprising culturing a cell as described in any one of embodiments 66-68 under conditions appropriate for polypeptide expression.

Embodiment 76. The method of any one of embodiments 71-75, further comprising isolating the polypeptide from the cell, cellular components and/or growth media.

Embodiment 77. The method of any one of embodiments 71-76, further comprising purifying the isolated polypeptide.

Embodiment 78. The method of embodiment 77, wherein the polypeptide is purified using an affinity column.

Embodiment 79. The method of embodiment 77 or 78, wherein the polypeptide is purified using gel filtration.

Embodiment 80. The method of any one of embodiments 77-79, wherein the purified protein comprises less than about 10% contaminants.

Embodiment 81. The method of any one of embodiments 71-80, wherein the polypeptide is capable of binding to ACE2.

Embodiment 82. A polypeptide produced by a method as described in any one of embodiments 71-81.

Certain Definitions

The term "nucleic acid" refers to deoxyribonucleotides or ribonucleotides and polymers thereof in either single- or double-stranded form, composed of monomers (nucleotides) containing a sugar, phosphate and a base which is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al. (1991) Nucl. Acids Res., 19:508; Ohtsuka et al. (1985) JBC, 260:2605; Rossolini et al. (1994) Mol. Cell. Probes, 8:91. A "nucleic acid fragment" is a fraction of a given nucleic acid molecule. Deoxyribonucleic acid (DNA) in the majority of organisms is the genetic material while ribonucleic acid (RNA) is involved in the transfer of information contained within DNA into proteins. The term "nucleotide sequence" refers to a polymer of DNA or RNA that can be single- or double-stranded, optionally containing synthetic, non-natural or altered nucleotide bases capable of incorporation into DNA or RNA polymers. The terms "nucleic acid," "nucleic acid molecule," "nucleic acid fragment," "nucleic acid sequence or segment," or "polynucleotide" may also be used interchangeably with gene, cDNA, DNA and RNA encoded by a gene.

By "portion" or "fragment," as it relates to a nucleic acid molecule, sequence or segment of the invention, when it is linked to other sequences for expression, is meant a sequence having at least 80 nucleotides, more preferably at least 150 nucleotides, and still more preferably at least 400 nucleotides. If not employed for expressing, a "portion" or "fragment" means at least 9, preferably 12, more preferably 15, even more preferably at least 20, consecutive nucleotides, e.g., probes and primers (oligonucleotides), corresponding to the nucleotide sequence of the nucleic acid molecules of the invention.

The term "amino acid," comprises the residues of the natural amino acids (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g. phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methyl-alanine, para-benzoylphenylalanine, phenylglycine, propargylglycine, sarcosine, and tert-butylglycine). The term also comprises natural and unnatural amino acids bearing a conventional amino protecting group (e.g. acetyl or benzyloxycarbonyl), as well as natural and unnatural amino acids protected at the carboxy terminus (e.g. as a ($C_1$-$C_6$) alkyl, phenyl or benzyl ester or amide; or as an α-methylbenzyl amide). Other suitable amino and carboxy protecting groups are known to those skilled in the art (See for example, T. W. Greene, *Protecting Groups In Organic Synthesis*; Wiley: New York, 1981, and references cited therein). An amino acid can be linked to the remainder of a conjugate of formula I through the carboxy terminus, the amino terminus, or through any other convenient point of attachment, such as, for example, through the sulfur of a cysteine.

The terms "protein," "peptide" and "polypeptide" are used interchangeably herein. Polypeptide sequences specifically recited herein are written with the amino terminus on the left and the carboxy terminus on the right.

The invention encompasses isolated or substantially purified nucleic acid or protein compositions. In the context of the present invention, an "isolated" or "purified" DNA molecule or an "isolated" or "purified" polypeptide is a DNA molecule or polypeptide that exists apart from its native environment and is therefore not a product of nature. An isolated DNA molecule or polypeptide may exist in a purified form or may exist in a non-native environment such as, for example, a transgenic host cell. For example, an "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein or polypeptide having less than about 30%, 20%, 10%, 5%, (by dry weight) of contaminating protein. When the protein of the invention, or biologically active portion thereof, is recombinantly produced, preferably culture medium represents less than about 30%, 20%, 10%, or 5% (by dry weight) of chemical precursors or non-protein-of-interest chemicals. Fragments and variants of the disclosed nucleotide sequences and proteins or partial-length proteins encoded thereby are also encompassed by the present invention. By "fragment" or "portion" is meant a full length or less than full length of the nucleotide sequence encoding, or the amino acid sequence of, a polypeptide or protein.

"Naturally occurring" is used to describe an object that can be found in nature as distinct from being artificially produced. For example, a protein or nucleotide sequence present in an organism (including a virus), which can be isolated from a source in nature and which has not been intentionally modified by man in the laboratory, is naturally occurring.

"Wild-type" refers to the normal gene, or organism found in nature without any known mutation.

A "variant" of a molecule is a sequence that is substantially similar to the sequence of the native molecule. For nucleotide sequences, variants include those sequences that, because of the degeneracy of the genetic code, encode the identical amino acid sequence of the native protein. Naturally occurring allelic variants such as these can be identified with the use of well-known molecular biology techniques, as, for example, with polymerase chain reaction (PCR) and hybridization techniques. Variant nucleotide sequences also include synthetically derived nucleotide sequences, such as those generated, for example, by using site-directed mutagenesis that encode the native protein, as well as those that encode a polypeptide having amino acid substitutions. Generally, nucleotide sequence variants of the invention will have at least 40, 50, 60, to 70%, e.g., preferably 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98%, sequence identity to the native (endogenous) nucleotide sequence.

"Conservatively modified variations" of a particular nucleic acid sequence refers to those nucleic acid sequences that encode identical or essentially identical amino acid sequences, or where the nucleic acid sequence does not encode an amino acid sequence, to essentially identical sequences. Because of the degeneracy of the genetic code, a large number of functionally identical nucleic acids encode any given polypeptide. For instance the codons CGT, CGC, CGA, CGG, AGA, and AGG all encode the amino acid arginine. Thus, at every position where an arginine is specified by a codon, the codon can be altered to any of the corresponding codons described without altering the encoded protein. Such nucleic acid variations are "silent variations" which are one species of "conservatively modified variations." Every nucleic acid sequence described herein which encodes a polypeptide also describes every possible silent variation, except where otherwise noted. One of skill will recognize that each codon in a nucleic acid (except ATG, which is ordinarily the only codon for methionine) can be modified to yield a functionally identical molecule by standard techniques. Accordingly, each "silent variation" of a nucleic acid which encodes a polypeptide is implicit in each described sequence.

"Recombinant DNA molecule" is a combination of DNA sequences that are joined together using recombinant DNA technology and procedures used to join together DNA sequences as described, for example, in Sambrook and Russell, Molecular Cloning: A Laboratory Manual, Cold Spring Harbor, NY: Cold Spring Harbor Laboratory Press ($3^{rd}$ edition, 2001).

The terms "heterologous DNA sequence," "exogenous DNA segment" or "heterologous nucleic acid," each refer to a sequence that originates from a source foreign to the particular host cell or, if from the same source, is modified from its original form. Thus, a heterologous gene in a host cell includes a gene that is endogenous to the particular host cell but has been modified. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides.

A "homologous" DNA sequence is a DNA sequence that is naturally associated with a host cell into which it is introduced.

The term "gene" is used broadly to refer to any segment of nucleic acid associated with a biological function. Genes include coding sequences and/or the regulatory sequences required for their expression. For example, gene refers to a nucleic acid fragment that expresses mRNA, functional RNA, or a specific protein, including its regulatory sequences. Genes also include nonexpressed DNA segments that, for example, form recognition sequences for other proteins. Genes can be obtained from a variety of sources, including cloning from a source of interest or synthesizing from known or predicted sequence information, and may include sequences designed to have desired parameters. In addition, a "gene" or a "recombinant gene" refers to a nucleic acid molecule comprising an open reading frame and including at least one exon and (optionally) an intron sequence. The term "intron" refers to a DNA sequence present in a given gene which is not translated into protein and is generally found between exons.

A "vector" is defined to include, inter alia, any viral vector, plasmid, cosmid, phage or binary vector in double or single stranded linear or circular form which may or may not be self-transmissible or mobilizable, and which can transform prokaryotic or eukaryotic host either by integration into the cellular genome or exist extrachromosomally (e.g., autonomous replicating plasmid with an origin of replication).

"Cloning vectors" typically contain one or a small number of restriction endonuclease recognition sites at which foreign DNA sequences can be inserted in a determinable fashion without loss of essential biological function of the vector, as well as a marker gene that is suitable for use in the identification and selection of cells transformed with the cloning vector. Marker genes typically include genes that provide tetracycline resistance, hygromycin resistance or ampicillin resistance.

"Expression cassette" as used herein means a DNA sequence capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The coding region usually codes for a protein of interest but may also code for a functional RNA of interest, for example antisense RNA or a nontranslated RNA, in the sense or antisense direction. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. The expression of the nucleotide sequence in the expression cassette may be under the control of a constitutive promoter or of an inducible promoter that initiates transcription only when the host cell is exposed to some particular external stimulus. In the case of a multicellular organism, the promoter can also be specific to a particular tissue or organ or stage of development.

Such expression cassettes will comprise the transcriptional initiation region of the invention linked to a nucleotide sequence of interest. Such an expression cassette is provided with a plurality of restriction sites for insertion of the gene of interest to be under the transcriptional regulation of the regulatory regions. The expression cassette may additionally contain selectable marker genes.

The term "RNA transcript" refers to the product resulting from RNA polymerase catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA" (mRNA) refers to the RNA that is without introns and that can be translated into protein by the cell. "cDNA" refers to a single- or a double-stranded DNA that is complementary to and derived from mRNA.

"Regulatory sequences" and "suitable regulatory sequences" each refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences include enhancers, promoters, translation leader sequences, introns, and polyadenylation signal sequences. They include natural and synthetic sequences as well as sequences that may be a combination of synthetic and natural sequences. As is noted above, the term "suitable regulatory sequences" is not limited to promoters. However, some suitable regulatory sequences useful in the present invention will include, but are not limited to constitutive promoters, tissue-specific promoters, development-specific promoters, inducible promoters and viral promoters.

"5' non-coding sequence" refers to a nucleotide sequence located 5' (upstream) to the coding sequence. It is present in the fully processed mRNA upstream of the initiation codon and may affect processing of the primary transcript to mRNA, mRNA stability or translation efficiency (Turner et al. (1995) Mol. Biotech. 3:225).

"3' non-coding sequence" refers to nucleotide sequences located 3' (downstream) to a coding sequence and include polyadenylation signal sequences and other sequences encoding regulatory signals capable of affecting mRNA processing or gene expression. The polyadenylation signal is usually characterized by affecting the addition of polyadenylic acid tracts to the 3' end of the mRNA precursor.

The term "translation leader sequence" refers to that DNA sequence portion of a gene between the promoter and coding sequence that is transcribed into RNA and is present in the fully processed mRNA upstream (5') of the translation start codon. The translation leader sequence may affect processing of the primary transcript to mRNA, mRNA stability or translation efficiency.

The term "mature" protein refers to a post-translationally processed polypeptide without its signal peptide. "Precursor" protein refers to the primary product of translation of an mRNA. "Signal peptide" refers to the amino terminal extension of a polypeptide, which is translated in conjunction with the polypeptide forming a precursor peptide and which is required for its entrance into the secretory pathway. The term "signal sequence" refers to a nucleotide sequence that encodes the signal peptide.

"Promoter" refers to a nucleotide sequence, usually upstream (5') to its coding sequence, which controls the expression of the coding sequence by providing the recognition for RNA polymerase and other factors required for proper transcription. "Promoter" includes a minimal promoter that is a short DNA sequence comprised of a TATA-box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence that can stimulate promoter activity and may be an innate element of the promoter or a heterologous element inserted to enhance the level or tissue specificity of a promoter. Promoters may be derived in their entirety from a native gene, or be composed of different elements derived from different promoters found in nature, or even be comprised of synthetic DNA segments. A promoter may also contain DNA sequences that are involved in the binding of protein factors that control the effectiveness of transcription initiation in response to physiological or developmental conditions.

The "initiation site" is the position surrounding the first nucleotide that is part of the transcribed sequence, which is also defined as position +1. With respect to this site all other sequences of the gene and its controlling regions are numbered. Downstream sequences (i.e. further protein encoding sequences in the 3' direction) are denominated positive, while upstream sequences (mostly of the controlling regions in the 5' direction) are denominated negative.

Promoter elements, particularly a TATA element, that are inactive or that have greatly reduced promoter activity in the absence of upstream activation are referred to as "minimal or core promoters." In the presence of a suitable transcription factor, the minimal promoter functions to permit transcription. A "minimal or core promoter" thus consists only of all basal elements needed for transcription initiation, e.g., a TATA box and/or an initiator.

"Constitutive expression" refers to expression using a constitutive or regulated promoter. "Conditional" and "regulated expression" refer to expression controlled by a regulated promoter.

As used herein, the term "operably linked" refers to a linkage of two elements in a functional relationship. For example, "operably linked" may refer to a linkage of polynucleotide (or polypeptide) elements in a functional relationship. A nucleic acid is "operably linked" when it is placed into a functional relationship with another nucleic acid sequence. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation. "Operably-linked" also refers to the association two chemical moieties so that the function of one is affected by the other, e.g., an arrangement of elements wherein the components so described are configured so as to perform their usual function.

"Expression" refers to the transcription and/or translation in a cell of an endogenous gene, transgene, as well as the transcription and stable accumulation of sense (mRNA) or functional RNA. In the case of antisense constructs, expression may refer to the transcription of the anti sense DNA only. Expression may also refer to the production of protein.

"Transcription stop fragment" refers to nucleotide sequences that contain one or more regulatory signals, such as polyadenylation signal sequences, capable of terminating transcription. Examples of transcription stop fragments are known to the art.

"Translation stop fragment" refers to nucleotide sequences that contain one or more regulatory signals, such as one or more termination codons in all three frames, capable of terminating translation. Insertion of a translation stop fragment adjacent to or near the initiation codon at the 5' end of the coding sequence will result in no translation or improper translation. Excision of the translation stop fragment by site-specific recombination will leave a site-specific sequence in the coding sequence that does not interfere with proper translation using the initiation codon.

"Homology" refers to the percent identity between two polynucleotides or two polypeptide sequences. Two DNA or polypeptide sequences are "homologous" to each other when the sequences exhibit at least about 75% to 85% (including 75%, 76%, 77%, 78%, 79%, 80%, 81%, 82%, 83%, 84%, and 85%), at least about 90%, or at least about 95% to 99% (including 95%, 96%, 97%, 98%, 99%) contiguous sequence identity over a defined length of the sequences.

The following terms are used to describe the sequence relationships between two or more sequences (e.g., nucleic acids, polynucleotides or polypeptides): (a) "reference sequence," (b) "comparison window," (c) "sequence identity," (d) "percentage of sequence identity," and (e) "substantial identity."

(a) As used herein, "reference sequence" is a defined sequence used as a basis for sequence comparison. A reference sequence may be a subset or the entirety of a specified sequence; for example, as a segment of a full length cDNA, gene sequence or peptide sequence, or the complete cDNA, gene sequence or peptide sequence.

(b) As used herein, "comparison window" makes reference to a contiguous and specified segment of a sequence, wherein the sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the sequence a gap penalty is typically introduced and is subtracted from the number of matches.

Methods of alignment of sequences for comparison are well known in the art. Thus, the determination of percent identity between any two sequences can be accomplished using a mathematical algorithm. Non-limiting examples of such mathematical algorithms are the algorithm of Myers and Miller (1988) CABIOS, 4:11; the local homology algorithm of Smith et al. (1981) Adv. Appl. Math. 2:482; the homology alignment algorithm of Needleman and Wunsch, (1970) JMB, 48:443; the search-for-similarity-method of Pearson and Lipman, (1988) Proc. Natl. Acad. Sci. USA, 85:2444; the algorithm of Karlin and Altschul, (1990) Proc. Natl. Acad. Sci. USA, 87:2264, modified as in Karlin and Altschul, (1993) Proc. Natl. Acad. Sci. USA, 90:5873.

Computer implementations of these mathematical algorithms can be utilized for comparison of sequences to determine sequence identity. Such implementations include, but are not limited to: CLUSTAL in the PC/Gene program (available from Intelligenetics, Mountain View, California); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wisconsin, USA). Alignments using these programs can be performed using the default parameters. The CLUSTAL program is well described by Higgins et al. (1988) Gene 73:237; Higgins et al. (1989) CABIOS 5:151; Corpet et al. (1988) Nucl. Acids Res. 16:10881; Huang et al. (1992) CABIOS 8:155; and Pearson et al. (1994) Meth. Mol. Biol. 24:307. The ALIGN program is based on the algorithm of Myers and Miller, supra. The BLAST programs of Altschul et al. (1990) JMB, 215:403; Nucl. Acids Res., 25:3389 (1990), are based on the algorithm of Karlin and Altschul supra.

Software for performing BLAST analyses is publicly available through the National Center for Biotechnology Information (available on the world wide web at ncbi.nlm-.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased.

Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

To obtain gapped alignments for comparison purposes, Gapped BLAST (in BLAST 2.0) can be utilized as described in Altschul et al. (1997) Nucleic Acids Res. 25:3389. Alternatively, PSI-BLAST (in BLAST 2.0) can be used to perform an iterated search that detects distant relationships between molecules. See Altschul et al., supra. When utilizing BLAST, Gapped BLAST, PSI-BLAST, the default parameters of the respective programs (e.g., BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. See the world wide web at ncbi.nlm.nih.gov. Alignment may also be performed manually by visual inspection.

For purposes of the present invention, comparison of sequences for determination of percent sequence identity to another sequence may be made using the Blast program (e.g., BlastN, version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

(c) As used herein, "sequence identity" or "identity" in the context of two nucleic acid or polypeptide sequences makes reference to a specified percentage of residues in the two sequences that are the same when aligned for maximum correspondence over a specified comparison window, as measured by sequence comparison algorithms or by visual inspection. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, California).

(d) As used herein, "percentage of sequence identity" means the value determined by comparing two optimally aligned sequences over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of sequences means that a polynucleotide comprises a sequence that has at least 70%, 71%, 72%, 73%, 74%, 75%, 76%, 77%, 78%, or 79%, at least 80%, 81%, 82%, 83%, 84%, 85%, 86%, 87%, 88%, or 89%, at least 90%, 91%, 92%, 93%, or 94%, and at least 95%, 96%, 97%, 98%, or 99% sequence identity, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 70%, at least 80%, 90%, at least 95%.

Another indication that nucleotide sequences are substantially identical is if two molecules hybridize to each other under stringent conditions (see below). Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70%, 71%, 72%, 73%, 74%, 75%, 76%, 77%, 78%, or 79%, 80%, 81%, 82%, 83%, 84%, 85%, 86%, 87%, 88%, or 89%, at least 90%, 91%, 92%, 93%, or 94%, or 95%, 96%, 97%, 98% or 99%, sequence identity to the reference sequence over a specified comparison window. Optimal alignment is conducted using the homology alignment algorithm of Needleman and Wunsch, J. Mol. Biol. 48:443 (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted above, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

By "variant" polypeptide is intended a polypeptide derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Such variants may results form, for example, genetic polymorphism or from human manipulation. Methods for such manipulations are generally known in the art.

Thus, the polypeptides of the invention may be altered in various ways including amino acid substitutions, deletions, truncations, and insertions. Methods for such manipulations are generally known in the art. For example, amino acid sequence variants of the polypeptides can be prepared by mutations in the DNA. Methods for mutagenesis and nucleotide sequence alterations are well known in the art. See, for example, Kunkel (1985) Proc. Natl. Acad. Sci. USA 82:488; Kunkel et al. (1987) Meth. Enzymol. 154:367; U.S. Pat. No. 4,873,192; Walker and Gaastra (1983) Techniques in Mol. Biol. (MacMillan Publishing Co., and the references cited therein. Guidance as to appropriate amino acid substitutions that do not affect biological activity of the protein of interest may be found in the model of Dayhoff et al., Atlas of Protein Sequence and Structure (Natl. Biomed. Res. Found. 1978). Conservative substitutions, such as exchanging one amino acid with another having similar properties, are preferred.

Thus, the genes and nucleotide sequences of the invention include both the naturally occurring sequences as well as mutant forms. Likewise, the polypeptides of the invention encompass naturally occurring proteins as well as variations and modified forms thereof. Such variants will continue to possess the desired activity. In certain embodiments, the deletions, insertions, and substitutions of the polypeptide sequence encompassed herein may not produce radical changes in the characteristics of the polypeptide. However, when it is difficult to predict the exact effect of the substitution, deletion, or insertion in advance of doing so, one skilled in the art will appreciate that the effect will be evaluated by routine screening assays.

Individual substitutions deletions or additions that alter, add or delete a single amino acid or a small percentage of amino acids (typically less than 5%, more typically less than 1%) in an encoded sequence are "conservatively modified variations," where the alterations result in the substitution of an amino acid with a chemically similar amino acid. Conservative substitution tables providing functionally similar amino acids are well known in the art. The following five groups each contain amino acids that are conservative substitutions for one another: Aliphatic: Glycine (G), Alanine (A), Valine (V), Leucine (L), Isoleucine (I); Aromatic: Phenylalanine (F), Tyrosine (Y), Tryptophan (W); Sulfur-containing: Methionine (M), Cysteine (C); Basic: Arginine (R), Lysine (K), Histidine (H); Acidic: Aspartic acid (D), Glutamic acid (E), Asparagine (N), Glutamine (Q). In addition, individual substitutions, deletions or additions which alter, add or delete a single amino acid or a small percentage of amino acids in an encoded sequence are also "conservatively modified variations."

The term "transformation" refers to the transfer of a nucleic acid fragment into the genome of a host cell, resulting in genetically stable inheritance. Host cells containing the transformed nucleic acid fragments are referred to as "transgenic" cells, and organisms comprising transgenic cells are referred to as "transgenic organisms".

"Transformed," "transgenic," "transduced" and "recombinant" refer to a host cell or organism into which a heterologous nucleic acid molecule has been introduced. The nucleic acid molecule can be stably integrated into the genome generally known in the art and are disclosed in Sambrook and Russell, supra. See also Innis et al., PCR Protocols, Academic Press (1995); and Gelfand, PCR Strategies, Academic Press (1995); and Innis and Gelfand, PCR Methods Manual, Academic Press (1999). Known methods of PCR include, but are not limited to, methods using paired primers, nested primers, single specific primers, degenerate primers, gene-specific primers, vector-specific primers, partially mismatched primers, and the like. For example, "transformed," "transformant," and "transgenic" cells have been through the transformation process and contain a foreign gene integrated into their chromosome. The term "untransformed" refers to normal cells that have not been through the transformation process.

"Genetically altered cells" denotes cells which have been modified by the introduction of recombinant or heterologous nucleic acids (e.g., one or more DNA constructs or their RNA counterparts) and further includes the progeny of such cells which retain part or all of such genetic modification.

As used herein, the term "derived" or "directed to" with respect to a nucleotide molecule means that the molecule has complementary sequence identity to a particular molecule of interest.

The terms "treat" and "treatment" refer to both therapeutic treatment and prophylactic or preventative measures, wherein the object is to prevent or slow down (lessen) an undesired physiological change or disorder. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The phrase "therapeutically effective amount" means an amount of a polypeptide of the present invention that (i) treats the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

As used herein, a "subject" is an animal, e.g., a mammal, e.g., a human, monkey, dog, cat, horse, cow, pig, goat, rabbit, or mouse.

The invention will now be illustrated by the following non-limiting Examples.

Example 1. Generation of Stable Cell Lines Expressing SARS-CoV2 RBD

The SARS-CoV-2 receptor-binding domain (RBD) is directly involved in the binding of SARS-CoV-2 to the host receptor ACE2. As described below, mammalian 293F cells were genetically modified using a lentivirus system to stably express a SARS-CoV-2 RBD polypeptide.

Materials and Methods

HEK293T cells were purchased from ATCC and 293F cells were purchased from Thermo Fisher Scientific.

Cloning

A construct encoding the following polypeptide, from N-terminus to C-terminus, was prepared: a tPA signal peptide sequence+a SARS-COV-2 RBD segment (SEQ ID NO:2)+8×His tag (SEQ ID NO: 6) (see, SEQ ID NO:4). The construct was cloned into a lentivirus vector (RBD plasmid) (see, FIGS. 1A-B; SEQ ID NO:1). Briefly, PCR was performed using a forward primer containing the tPA sequence, a reverse primer containing a linker and His tag, and a high fidelity DNA polymerase. The PCR product was purified and inserted into a double restrictively digested (XbaI and SalI) lentivirus vector using HiFi assembly master mix. The ligation products were transformed into DH5α competent cells. Single bacterial colonies were picked for plasmids extraction. The plasmids were confirmed by DNA sequencing, and the correct constructs were used for further experiments.

Preparation of Lentivirus Particles

HEK293T cells ($5*10^5$ cells per well in 6 wells plate) were incubated at 37° C., 5% $CO_2$ overnight. The transfection was performed the next day using Lipofectamine 3000. Briefly, the RBD plasmid (1.5 ug) was mixed with 750 ng psPAX2 packaging plasmid and 250 ng pMD2.G envelope plasmid to 100 ul serum-free OPTI-MEN in a polypropylene tube. 5 ul P3000 was added to the plasmid mixture while diluting 5 ul lipofectamine 3000 with another 100 ul serum-free OPTI-MEN in another polypropylene tube. The plasmid cocktail was pipetted directly into the liquid containing the lipofectamine and then mixed by swirling or gently flicking the tube. The mixture was incubated for 10-15 minutes at room temperature and then the transfection mixture was gently added dropwise to the cells (the HEK293T cells should be 50-80% confluent). The cells were incubated at 37° C., 5% CO 2 for 24-48 hours. Media from the cells was harvested and transferred to a polypropylene storage tube. The harvested media, which contains the lentiviral particles, was stored at 4° C. (Note: for handling the lentivirus, the BSL2+ environment and following safety procedures are required).

Infecting 293F Cells and Selection 30 ml of 293F cells ($1*10^6$ cells/ml) were placed into a 125 ml shaking flask and Hexadimethrine bromide (polybrene) was added into media with a final concentration of 8 ug/ml. 1 ml of the harvested lentiviral particle solution from the above step was added to the flask. The cells were incubated at 37° C., 8% $CO_2$ in a shaking incubator overnight. Fresh 293F expression media was added the next morning; puromycin (1 ug/ml) was included in the media for selection. After two days, cells which contain the RBD gene will survive, while cells that do not contain the RBD gene will not survive. Fresh puromycin-containing media was provided as needed every few days. After almost one week, all the cells were selected and had turned into the RBD expressing cells.

Protein Purification

The 293F/RBD cells (see, above) were grown in 293 FreeStyle expression medium cultured at 37° C. with 8% $CO_2$ and 150 rpm in the $CO_2$ shaker. The cells were seeded in a flask at $1\times10^6$ cells/ml. 4 days later the supernatants were harvested and the protein was purified by Nickel column and gel filtration column. Briefly, the supernatants were concentrated after harvest, and the buffer was exchanged with phosphate-buffered saline into 100 ml to remove EDTA. Then the samples were loaded though a 5 ml Nickel column at 3 ml/min. The column which contains the His tagged protein was eluted by gradient imidazole phosphate buffer; the target protein came out at 100-180 mM imidazole concentration. SDS-PAGE was run to check purity. The proteins were concentrated and loaded into a gel filtration column and eluted by Tris buffer (20 mM Tris pH 7.4 and 200 mM NaCl). The right size peak samples were collected and concentrated into a stock concentration and flash frozen for stock.

ACE2 Binding Assay

Human ACE2-Fc (4 ug/ml) was coated on ELISA plate at 4° C. overnight and then blocked with 3% BSA. RBD polypeptide at different dilutions was added, and incubation of the samples lasted for 1 hour at 37° C. After three washes with PBS buffer, HRP conjugated anti-His antibody (1:5, 000, Santa Cruz, CA) was added, and incubation of the samples lasted for 1 hour at 37° C. ELISA substrate 3,3',5,5'-Tetramethylbenzidine (TMB) (Sigma, St. Louis, MO) was added, and the reaction was stopped using H2SO4 (1 N). ELISA signal was detected using a plate reader (Tecan, San Jose, CA) at 450 nm.

Results

Figure 1B:
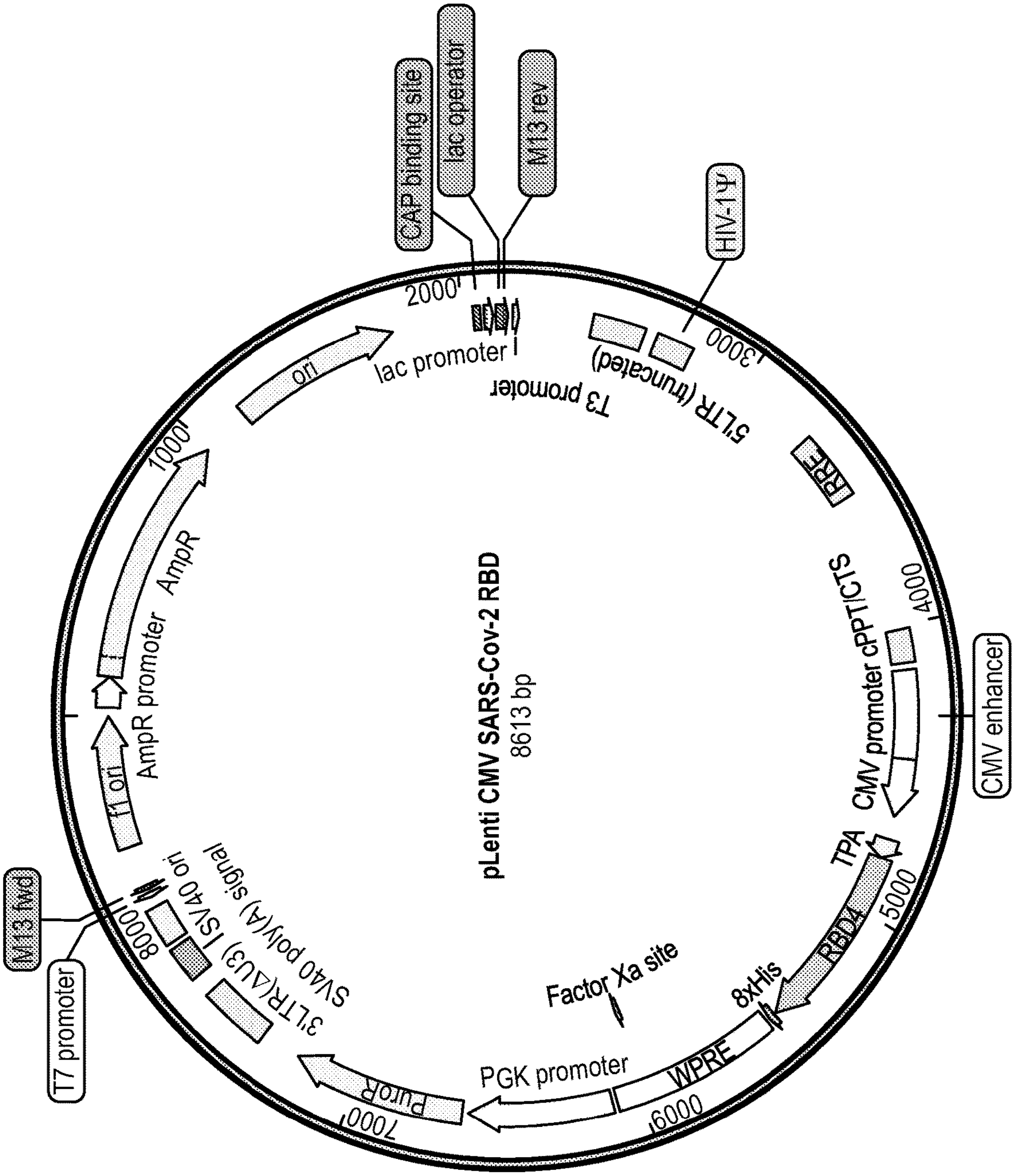
Figure 2A:
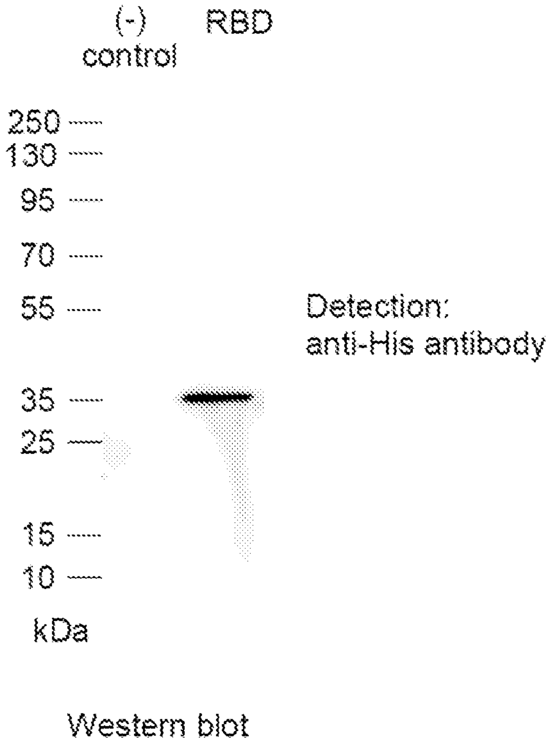
FIGS. 2A-2B. Recombinant SARS-CoV-2 RBD protein purified on a Nickel column and gel filtration column.
Figure 2B:
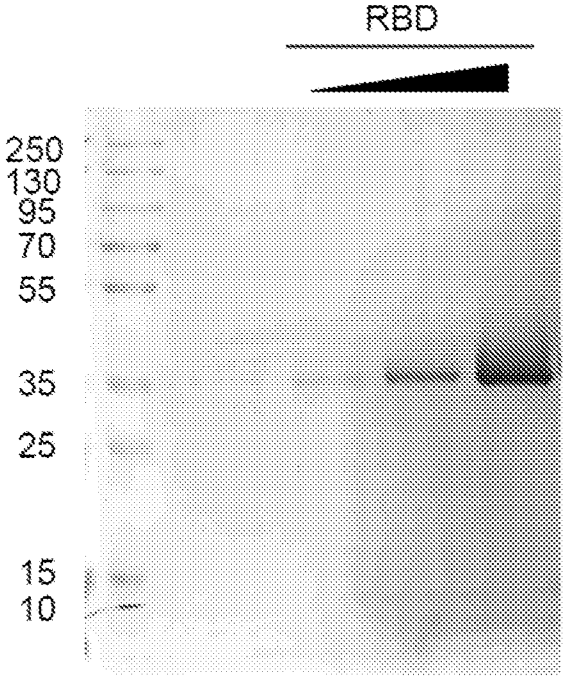
Figure 3:
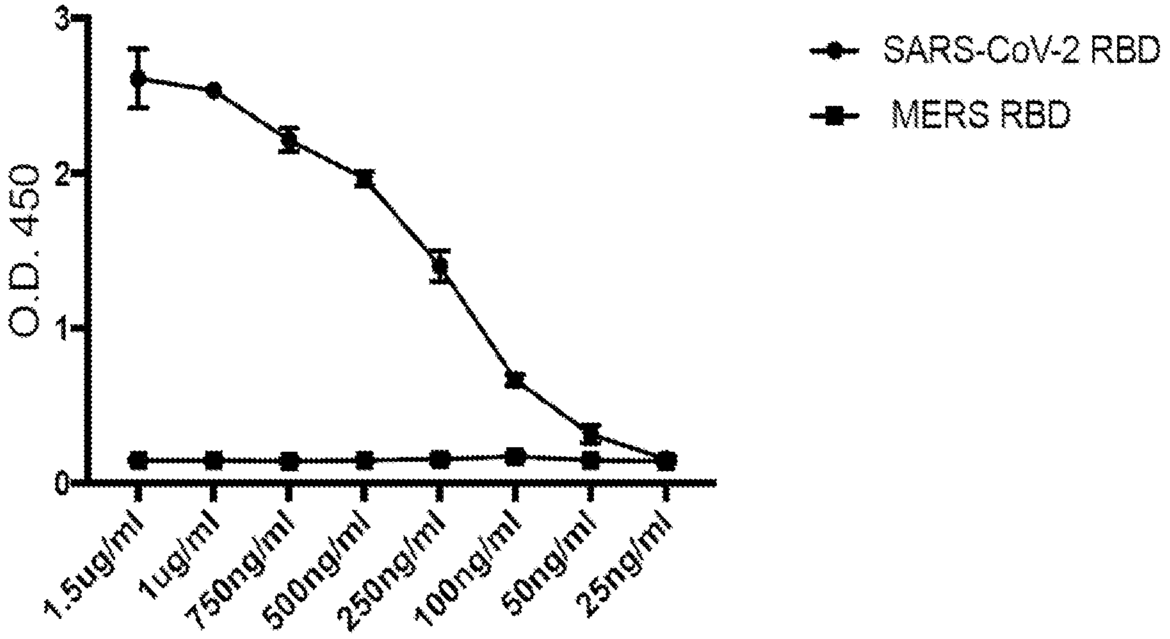
FIG. 3. SARS-CoV-2 RBD protein binding to human ACE2 with high affinity.

Mammalian 293F cells were genetically modified using a lentivirus system to stably express a SARS-COV-2 RBD polypeptide. Specifically, the expressed recombinant polypeptide comprised a SARS-COV-2 RBD segment (SEQ ID NO:2) and a C-terminal 8×His tag (SEQ ID NO: 6) (FIGS. 1A-B). The protein was purified using both a Nickel column and a gel filtration column (see, FIGS. 2A-2B). The final purified recombinant protein was shown to be biologically active, binding to human ACE2 with high affinity (FIG. 3).

Compared to transiently transfected mammalian cells, the SARS-CoV-2 RBD expressed from stably transfected mammalian cells can be quickly obtained, has a high yield and high purity, and is correctly folded and biologically active. Additionally, the SARS-CoV-2 RBD expressed from stably transfected mammalian cells has correctly added glycans and is more antigenic (e.g., is better suited for antigenic assays) as compared to protein generated in other expression systems, such as insect cells. This system also easily allows production of SARS-CoV-2 RBD to be scaled up to suite industrial and commercial uses while maintaining the high quality of the product.

Example 2. Method for Generating and Using an Enzyme-Linked Immunosorbent Assay (ELISA) Plate for a Serological Antibody Test A clear polystyrene microplate optimized for antigen-down ELISA is used. The surface chemistry of the polystyrene microplate is suitable for probing serum samples to mitigate non-specific immunoglobulin binding, while maintaining reasonable capacity for satisfactory antigen coating. During microplate manufacturing, the surface of the microplate can be treated with corona discharge irradiation processes that generate high-energy oxygen ions that can be incorporated into the polystyrene polymer chain, conferring hydrophilicity to the plate surface. In this non-limiting example, the microplate exhibits intermediate hydrophobicity and IgG binding power. However, a microplate with higher hydrophobicity or higher hydrophilicity can be selected.

Bicarbonate-carbonate based buffer is used as the coating buffer. The plate is coated with 10 μg/ml of the polypeptide in pH 9.6 bicarbonate-carbonate based buffer (e.g., 100 μl per well) overnight (e.g., at 4° C. in a moist chamber). Then the plates are washed three times with washing buffer (e.g., PBS with 0.05% Tween20). Non-specific binding can be blocked by adding 200 μL blocking buffer (e.g., PBS with 1% casein) per well for 1 hour at 37° C.

Serial dilutions of serum samples are conducted in 1% casein-PBS blocking buffer. Diluted serum samples are added to the microplate wells and incubated (100 μL per well) for 1.5 hours at 37° C. Plates are washed four times with washing buffer. Detection agents anti-human IgG-HRP or anti-human IgM-HRP are diluted in blocking buffer and 100 μL of diluted detection buffer is added to each well. The detection agent is incubated at room temperature for 1.5 hours followed by four times of washing. 0-phenylenediamine (OPD) substrate (100 μL per well) is added and developed for 15 min at room temperature followed by addition of 100 stop solution (2M HCL). The optical density is determined using an Absorbance Microplate Reader.

TABLE 1

| SEQ ID NO: | Sequences | Comment |
|---|---|---|
| 1 | *ATGGACGCCATGAAGAGGGGCCTGTGCTGCGTGCTGCTGCTGTGCGGC*<br>*GCCGTGTTCGTGAGCGCCAGC***CGCGTGCAGCCAACCGAGAGCATCGTG**<br>**CGCTTCCCCAATATCACCAACCTGTGCCCATTCGGCGAGGTGTTCAAC**<br>**GCTACCAGGTTCGCCAGCGTGTACGCTTGGAATCGCAAGCGCATCTCC**<br>**AACTGCGTGGCCGACTACAGCGTGCTGTACAACTCCGCCAGCTTCTCC**<br>**ACCTTCAAGTGCTACGGCGTGTCCCCCACCAAGCTGAATGATCTGTGC**<br>**TTCACCAACGTGTACGCCGATAGCTTCGTGATCAGGGGCGACGAGGTG**<br>**CGCCAGATCGCTCCAGGACAGACCGGCAAGATCGCTGACTACAATTAC**<br>**AAGCTGCCCGACGATTTCACCGGCTGCGTGATCGCCTGGAACTCCAAC**<br>**AATCTGGATAGCAAAGTGGGCGGCAACTACAATTACCTGTACCGCCTG**<br>**TTCCGCAAGTCCAATCTGAAGCCATTCGAGCGCGACATCTCCACCGAG**<br>**ATCTACCAGGCTGGAAGCACCCCATGCAATGGAGTGGAGGGCTTCAAC**<br>**TGCTACTTCCCCCTGCAGAGCTACGGCTTCCAGCCAACCAACGGAGTG**<br>**GGATACCAGCCATACAGGGTGGTGGTGCTGTCCTTCGAGCTGCTGCAC**<br>**GCTCCAGCTACCGTGTGCGGACCAAAGAAGAGCACCAATCTGGTGAAG**<br>GGATCC**CACCATCACCATCACCATCACCAT**TAG | Nucleic acid encoding SEQ ID NO: 4: nucleotides in italics encode the tPA signal peptide; nucleotides in bold encode the SARS-CoV-2 RBD; the encoded linker is underlined; the nucleotides in bold/underline encode the His tag; and the shaded nucleotides represent the stop codon. |
| 2 | RVQPTESIVRFPNITNLCPFGEVFNATRFASVYAWNRKRISNCVADYS<br>VLYNSASFSTFKCYGVSPTKLNDLCFTNVYADSFVIRGDEVRQIAPGQ<br>TGKIADYNYKLPDDFTGCVIAWNSNNLDSKVGGNYNYLYRLFRKSNLK<br>PFERDISTEIYQAGSTPCNGVEGFNCYFPLQSYGFQPTNGVGYQPYRV<br>VVLSFELLHAPATVCGPKKSTNLVK | Protein sequence of SARS-Cov-2 RBD segment (aa 319 to 535) |
| 3 | RVQPTESIVRFPNITNLCPFGEVFNATRFASVYAWNRKRISNCVADYS<br>VLYNSASFSTFKCYGVSPTKLNDLCFTNVYADSFVIRGDEVRQIAPGQ<br>TGKIADYNYKLPDDFTGCVIAWNSNNLDSKVGGNYNYLYRLFRKSNLK<br>PFERDISTEIYQAGSTPCNGVEGFNCYFPLQSYGFQPTNGVGYQPYRV<br>VVLSFELLHAPATVCGPKKSTNLVKGSHHHHHHHH | Protein sequence for: SARS-CoV-2 RBD segment + GS linker + His 8 tag (SEQ ID NO: 6) |
| 4 | MDAMKRGLCCVLLLCGAVFVSASRVQPTESIVRFPNITNLCPFGEVFN<br>ATRFASVYAWNRKRISNCVADYSVLYNSASFSTFKCYGVSPTKLNDLC<br>FTNVYADSFVIRGDEVRQIAPGQTGKIADYNYKLPDDFTGCVIAWNSN<br>NLDSKVGGNYNYLYRLFRKSNLKPFERDISTEIYQAGSTPCNGVEGFN<br>CYFPLQSYGFQPTNGVGYQPYRVVVLSFELLHAPATVCGPKKSTNLVK<br>GSHHHHHHHH | Protein sequence for: tPA signal peptide + SARS-CoV-2 RBD segment + GS linker + His 8 tag (SEQ ID NO: 6) |
| 5 | EKGIYQTSNFRVQPTESIVRFPNITNLCPFGEVFNATRFASVYAWNRK<br>RISNCVADYSVLYNSASFSTFKCYGVSPTKLNDLCFTNVYADSFVIRG<br>DEVRQIAPGQTGKIADYNYKLPDDFTGCVIAWNSNNLDSKVGGNYNYL<br>YRLFRKSNLKPFERDISTEIYQAGSTPCNGVEGFNCYFPLQSYGFQPT<br>NGVGYQPYRVVVLSFELLHAPATVCGPKKSTNLVKNKCVNFNFNG | Certain protein sequence comprising SARS-CoV-2 RBD segment |

TABLE 1-continued

| SEQ ID NO: | Sequences | Comment |
|---|---|---|
| 6 | HHHHHHHH | His 8 tag |
| 7 | MDAMKRGLCCVLLLCGAVFVSAS | tPA signal peptide |
| 8 | ATGTTTGTCTTCCTGGTCCTGCTGCCTCTGGTCTCGTCTCAGTGCGTG<br>AACCTGACTACTAGAACCCAGCTGCCTCCTGCCTATACTAACTCCTTC<br>ACCCGCGGCGTGTACTACCCAGACAAGGTGTTCCGCAGCTCCGTGCTG<br>CACTCCACCCAGGATCTGTTCCTGCCCTTCTTCAGCAACGTGACCTGG<br>TTCCACGCCATCCACGTGAGCGGCACCAATGGCACCAAGCGGTTCGAC<br>AATCCCGTGCTGCCATTCAACGATGGCGTGTACTTCGCCTCCACCGAG<br>AAGAGCAACATCATCCGCGGCTGGATCTTCGGCACCACCCTGGACTCC<br>AAGACCCAGAGCCTGCTGATCGTGAACAATGCCACCAACGTGGTCATC<br>AAGGTGTGCGAGTTCCAGTTCTGCAATGATCCATTCCTGGGCGTGTAC<br>TACCACAAGAACAATAAGTCCTGGATGGAGAGCGAGTTCCGCGTGTAC<br>AGCTCCGCCAACAATTGCACCTTCGAGTACGTGTCCCAGCCCTTCCTG<br>ATGGACCTGGAGGGCAAGCAGGGCAATTTCAAGAACCTGCGCGAGTTC<br>GTGTTCAAGAATATCGATGGCTACTTCAAGATCTACTCCAAGCACACC<br>CCCATCAACCTGGTGCGCGACCTGCCACAGGGCTTCAGCGCCCTGGAG<br>CCACTGGTGGATCTGCCAATCGGCATCAACATCACCAGGTTCCAGACC<br>CTGCTGGCCCTGCACCGCAGCTACCTGACCCCAGGCGACAGCTCCAGC<br>GGATGGACCGCTGGAGCTGCTGCCTACTACGTGGGCTACCTGCAGCCC<br>CGCACCTTCCTGCTGAAGTACAACGAGAATGGCACCATCACCGACGCC<br>GTGGATTGCGCCCTGGATCCACTGTCCGAGACAAAGTGCACCCTGAAG<br>AGCTTCACCGTGGAGAAGGGCATCTACCAGACCTCCAATTTCCGCGTG<br>CAGCCAACCGAGAGCATCGTGCGCTTCCCCAATATCACCAACCTGTGC<br>CCATTCGGCGAGGTGTTCAACGCTACCAGGTTCGCCAGCGTGTACGCT<br>TGGAATCGCAAGCGCATCTCCAACTGCGTGGCCGACTACAGCGTGCTG<br>TACAACTCCGCCAGCTTCTCCACCTTCAAGTGCTACGGCGTGTCCCCC<br>ACCAAGCTGAATGATCTGTGCTTCACCAACGTGTACGCCGATAGCTTC<br>GTGATCAGGGGCGACGAGGTGCGCCAGATCGCTCCAGGACAGACCGGC<br>AAGATCGCTGACTACAATTACAAGCTGCCCGACGATTTCACCGGCTGC<br>GTGATCGCCTGGAACTCCAACAATCTGGATAGCAAAGTGGGCGGCAAC<br>TACAATTACCTGTACCGCCTGTTCCGCAAGTCCAATCTGAAGCCATTC<br>GAGCGCGACATCTCCACCGAGATCTACCAGGCTGGAAGCACCCCATGC<br>AATGGAGTGGAGGGCTTCAACTGCTACTTCCCCCTGCAGAGCTACGGC<br>TTCCAGCCAACCAACGGAGTGGGATACCAGCCATACAGGGTGGTGGTG<br>CTGTCCTTCGAGCTGCTGCACGCTCCAGCTACCGTGTGCGGACCAAAG<br>AAGAGCACCAATCTGGTGAAGAACAAGTGCGTGAACTTCAATTTCAAC<br>GGCCTGACCGGAACCGGCGTGCTGACCGAGTCCAACAAGAAGTTCCTG<br>CCATTCCAGCAGTTCGGAAGGGACATCGCTGATACCACCGACGCCGTG<br>CGCGACCCACAGACCCTGGAGATCCTGGATATCACCCCATGCTCCTTC<br>GGCGGCGTGAGCGTGATCACCCCAGGAACCAATACCAGCAACCAGGTG<br>GCCGTGCTGTACCAGGACGTGAATTGCACCGAGGTGCCAGTGGCTATC<br>CACGCTGATCAGCTGACCCCAACCTGGCGCGTGTACAGCACCGGATCC<br>AACGTGTTCCAGACCCGCGCCGGATGCCTGATCGGAGCTGAGCACGTG<br>AACAATTCCTACGAGTGCGACATCCCAATCGGAGCTGGAATCTGCGCC<br>AGCTACCAGACCCAGACCAACTCCCCAAGGAGGGCTCGCAGCGTGGCC<br>AGCCAGTCCATCATCGCCTACACCATGTCCCTGGGCGCCGAGAATAGC<br>GTGGCCTACAGCAACAATTCCATCGCCATCCCAACCAACTTCACCATC<br>TCCGTGACCACCGAGATCCTGCCCGTGTCCATGACCAAGACCAGCGTG<br>GACTGCACCATGTACATCTGCGGCGATTCCACCGAGTGCAGCAACCTG<br>CTGCTGCAGTACGGCAGCTTCTGCACCCAGCTGAATCGCGCCCTGACC<br>GGAATCGCTGTGGAGCAGGATAAGAACACCCAGGAGGTGTTCGCCCAG<br>GTGAAGCAGATCTACAAGACCCCCCCAATCAAGGACTTCGGCGGCTTC<br>AATTTCAGCCAGATCCTGCCCGATCCAAGCAAGCCCTCCAAGCGCAGC<br>TTCATCGAGGACCTGCTGTTCAACAAGGTGACCCTGGCCGATGCCGGC<br>TTCATCAAGCAGTACGGCGATTGCCTGGGCGACATCGCTGCCCGCGAC<br>CTGATCTGCGCCCAGAAGTTCAATGGCCTGACCGTGCTGCCACCACTG<br>CTGACCGATGAGATGATCGCTCAGTACACCTCCGCCCTGCTGGCCGGA<br>ACCATCACCAGCGGATGGACCTTCGGCGCTGGAGCCGCCCTGCAGATC<br>CCCTTCGCCATGCAGATGGCCTACCGCTTCAACGGCATCGGCGTGACC<br>CAGAATGTGCTGTACGAGAACCAGAAGCTGATCGCCAATCAGTTCAAC<br>TCCGCCATCGGCAAGATCCAGGACTCCCTGTCCAGCACCGCCAGCGCC<br>CTGGGCAAGCTGCAGGATGTGGTGAATCAGAACGCCCAGGCCCTGAAT<br>ACCCTGGTGAAGCAGCTGTCCAGCAACTTCGGCGCCATCTCCAGCGTG<br>CTGAATGATATCCTGAGCCGCCTGGACAAGGTGGAGGCTGAGGTGCAG<br>ATCGATAGGCTGATCACCGGCCGCCTGCAGTCCCTGCAGACCTACGTG<br>ACCCAGCAGCTGATCAGGGCTGCTGAGATCAGGGCCAGCGCCAATCTG<br>GCTGCTACCAAGATGTCCGAGTGCGTGCTGGGACAGAGCAAGAGGGTG<br>GACTTCTGCGGCAAGGGCTACCACCTGATGTCCTTCCCACAGAGCGCC<br>CCACACGGAGTGGTGTTCCTGCACGTGACCTACGTGCCAGCCCAGGAG<br>AAGAACTTCACCACCGCTCCAGCTATCTGCCACGATGGCAAGGCTCAC<br>TTCCCACGCGAGGGCGTGTTCGTGTCCAACGGCACCCACTGGTTCGTG<br>ACCCAGCGCAATTTCTACGAGCCCCAGATCATCACCACCGACAATACC<br>TTCGTGAGCGGCAACTGCGACGTGGTCATCGGAATCGTGAACAATACC | SARS-CoV-2 Spike nucleic acid sequence |

TABLE 1-continued

| SEQ ID NO: | Sequences | Comment |
|---|---|---|
| | GTGTACGATCCCCTGCAGCCAGAGCTGGACTCCTTCAAGGAGGAGCTG<br>GATAAGTACTTCAAGAATCACACCAGCCCCGACGTGGATCTGGGCGAC<br>ATCTCCGGCATCAATGCCAGCGTGGTGAACATCCAGAAGGAGATCGAC<br>CGCCTGAACGAGGTGGCCAAGAATCTGAACGAGTCCCTGATCGATCTG<br>CAGGAGCTGGGCAAGTACGAGCAGTACATCAAGTGGCCATGGTACATC<br>TGGCTGGGCTTCATCGCCGGCCTGATCGCCATCGTGATGGTGACCATC<br>ATGCTGTGCTGCATGACCTCCTGCTGCAGCTGCCTGAAGGGCTGCTGC<br>TCCTGCGGCAGCTGCTGCAAGTTCGATGAGGACGATAGCGAGCCCGTG<br>CTGAAGGGCGTCAAACTGCACTATACA | |
| 9 | MFVFLVLLPLVSSQCVNLTTRTQLPPAYTNSFTRGVYYPDKVFRSSVL<br>HSTQDLFLPFFSNVTWFHAIHVSGTNGTKRFDNPVLPFNDGVYFASTE<br>KSNIIRGWIFGTTLDSKTQSLLIVNNATNVVIKVCEFQFCNDPFLGVY<br>YHKNNKSWMESEFRVYSSANNCTFEYVSQPFLMDLEGKQGNFKNLREF<br>VFKNIDGYFKIYSKHTPINLVRDLPQGFSALEPLVDLPIGINITRFQT<br>LLALHRSYLTPGDSSSGWTAGAAAYYVGYLQPRTFLLKYNENGTITDA<br>VDCALDPLSETKCTLKSFTVEKGIYQTSNFRVQPTESIVRFPNITNLC<br>PFGEVFNATRFASVYAWNRKRISNCVADYSVLYNSASFSTFKCYGVSP<br>TKLNDLCFTNVYADSFVIRGDEVRQIAPGQTGKIADYNYKLPDDFTGC<br>VIAWNSNNLDSKVGGNYNYLYRLFRKSNLKPFERDISTEIYQAGSTPC<br>NGVEGFNCYFPLQSYGFQPTNGVGYQPYRVVVLSFELLHAPATVCGPK<br>KSTNLVKNKCVNFNFNGLTGTGVLTESNKKFLPFQQFGRDIADTTDAV<br>RDPQTLEILDITPCSFGGVSVITPGTNTSNQVAVLYQDVNCTEVPVAI<br>HADQLTPTWRVYSTGSNVFQTRAGCLIGAEHVNNSYECDIPIGAGICA<br>SYQTQTNSPRRARSVASQSIIAYTMSLGAENSVAYSNNSIAIPTNFTI<br>SVTTEILPVSMTKTSVDCTMYICGDSTECSNLLLQYGSFCTQLNRALT<br>GIAVEQDKNTQEVFAQVKQIYKTPPIKDFGGFNFSQILPDPSKPSKRS<br>FIEDLLFNKVTLADAGFIKQYGDCLGDIAARDLICAQKFNGLTVLPPL<br>LTDEMIAQYTSALLAGTITSGWTFGAGAALQ1PFAMQMAYRFNGIGVT<br>QNVLYENQKLIANQFNSAIGKIQDSLSSTASALGKLQDVVNQNAQALN<br>TLVKQLSSNFGAISSVLNDILSRLDKVEAEVQIDRLITGRLQSLQTYV<br>TQQLIRAAEIRASANLAATKMSECVLGQSKRVDFCGKGYHLMSFPQSA<br>PHGWFLHVTYVPAQEKNFTTAPAlCHDGKAHFPREGVFVSNGTHWFV<br>TQRNFYEPQIITTDNTFVSGNCDVVIGIVNNTVYDPLQPELDSFKEEL<br>DKYFKNHTSPDVDLGDISGINASVVNIQKEIDRLNEVAKNLNESLIDL<br>QELGKYEQYIKWPWYIWLGFIAGLIAIVMVTIMLCCMTSCCSCLKGCC<br>SCGSCCKFDEDDSEPVLKGVKLHYT | SARS-CoV-2 Spike amino acid sequence |
| 10 | FPNITNLCPFGEVFNATRFASVYAWNRKRISNCVADYSVLYNSASFST<br>FKCYGVSPTKLNDLCFTNVYADSFVIRGDEVRQIAPGQTGKIADYNYK<br>LPDDFTGCVIAWNSNNLDSKVGGNYNYLYRLFRKSNLKPFERDISTEI<br>YQAGSTPCNGVEGFNCYFPLQSYGFQPTNGVGYQPYRVVVLSFELLHA<br>PATVC | SEQ ID NO:2 without first 10 or last 10 residues; Protein sequence of SARS-CoV-2 RBD segment (aa 329 to 525) |
| 11 | RVQPTESIVR | First 10 residues of SEQ ID NO: 2; Protein sequence of SARS-CoV-2 RBD segment (aa 319-328) |
| 12 | GPKKSTNLVK | Last 10 residues of SEQ ID NO:2; Protein sequence of SARS-CoV-2 RBD segment (aa 526-535) |
| 13 | EKGIYQTSNF | First 10 residues of SEQ ID NO:5; Protein sequence of SARS-CoV-2 RBD segment (aa 309-318) |

TABLE 1-continued

| SEQ ID NO: | Sequences | Comment |
|---|---|---|
| 14 | NKCVNFNFNG | Last 10 residues of SEQ ID NO:5; Protein sequence of SARS-CoV-2 RBD segment (aa 536-545) |

All publications, patents and patent applications cited herein are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and "or" and similar referents in the context of describing the invention are to be construed to cover both the singular and the plural, unless otherwise indicated herein or clearly contradicted by context. Thus, for example, reference to "a subject polypeptide" includes a plurality of such polypeptides and reference to "the agent" includes reference to one or more agents and equivalents thereof known to those skilled in the art, and so forth.

The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventor for carrying out the invention. Variations of those embodiments may become apparent to those of ordinary skill in the art upon reading the foregoing description. The inventor expects skilled artisans to employ such variations as appropriate, and the inventor intends for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

With respect to ranges of values, the invention encompasses each intervening value between the upper and lower limits of the range to at least a tenth of the lower limit's unit, unless the context clearly indicates otherwise. Further, the invention encompasses any other stated intervening values. Moreover, the invention also encompasses ranges excluding either or both of the upper and lower limits of the range, unless specifically excluded from the stated range.

Further, all numbers expressing quantities of ingredients, reaction conditions, % purity, polypeptide and polynucleotide lengths, and so forth, used in the specification and claims, are modified by the term "about," unless otherwise indicated. Accordingly, the numerical parameters set forth in the specification and claims are approximations that may vary depending upon the desired properties of the present invention. At the very least, and not as an attempt to limit the application of the doctrine of equivalents to the scope of the claims, each numerical parameter should at least be construed in light of the number of reported significant digits, applying ordinary rounding techniques. Nonetheless, the numerical values set forth in the specific examples are reported as precisely as possible. Any numerical value, however, inherently contains certain errors from the standard deviation of its experimental measurement.

Unless defined otherwise, the meanings of all technical and scientific terms used herein are those commonly understood by one of skill in the art to which this invention belongs. One of skill in the art will also appreciate that any methods and materials similar or equivalent to those described herein can also be used to practice or test the invention. Further, all publications mentioned herein are incorporated by reference in their entireties.

What is claimed is:

1. An isolated or purified polypeptide comprising a SARS-COV-2 receptor binding domain (RBD) linked directly or through a linker group to a peptide tag, wherein the peptide tag is linked to the C-terminus of the RBD, and wherein:

[I] the SARS-COV-2 RBD consists of the amino acid sequence as set forth in SEQ ID NO: 2;

[II] the SARS-COV-2 RBD consists of the amino acid sequence as set forth in SEQ ID NO: 5; or

[III] the SARS-COV-2 RBD consists of the amino acid sequence as set forth in SEQ ID NO: 10.

2. The polypeptide of claim 1, wherein the SARS-COV-2 RBD consists of the amino acid sequence as set forth in SEQ ID NO:2.

3. The polypeptide of claim 1, wherein the peptide tag is an affinity tag.

4. The polypeptide of claim 1, wherein the polypeptide further comprises a signal peptide sequence, wherein the signal peptide sequence is operably linked to the SARS-COV-2 RBD.

5. The polypeptide of claim 1, wherein the polypeptide comprises the amino acid sequence as set forth in SEQ ID NO:3 or SEQ ID NO:4.

6. A composition comprising the polypeptide of claim 1 and a carrier.

7. The polypeptide of claim 3, wherein the affinity tag is a poly(His) tag, FLAG, 3×FLAG, c-Myc, or a hemagglutinin tag.

8. The polypeptide of claim 3, wherein the affinity tag is a 8×His tag.

* * * * *